US012629468B2

(12) United States Patent
Rucinski et al.

(10) Patent No.: US 12,629,468 B2
(45) Date of Patent: May 19, 2026

(54) DEVICES AND METHODS FOR DELIVERING SYNERGISTIC ACTIVE AGENTS TO TARGET SITES

(71) Applicant: IRRIMAX Corporation, Lawrenceville, GA (US)

(72) Inventors: Paul Rucinski, Ocklawaha, FL (US); Michael A. Gil, Peachtree Corners, GA (US); Venkata Katragadda, Marietta, GA (US)

(73) Assignee: IRRIMAX Corporation, Lawrenceville, GA (US)

( * ) Notice: Subject to any disclaimer, the term of this patent is extended or adjusted under 35 U.S.C. 154(b) by 334 days.

(21) Appl. No.: 18/401,049

(22) Filed: Dec. 29, 2023

(65) Prior Publication Data

US 2025/0213777 A1 Jul. 3, 2025

(51) Int. Cl.
*A61M 3/02* (2006.01)
*A61M 35/00* (2006.01)

(52) U.S. Cl.
CPC ........ *A61M 3/0262* (2013.01); *A61M 3/0279* (2013.01); *A61M 35/003* (2013.01)

(58) Field of Classification Search
CPC . A61M 3/0262; A61M 3/0279; A61M 35/003
See application file for complete search history.

(56) References Cited

U.S. PATENT DOCUMENTS

| | | | | |
|---|---|---|---|---|
| 7,662,125 B2 * | 2/2010 | Rucinski | A61M 35/003 424/45 |
| 7,959,617 B2 * | 6/2011 | Rucinski | A61M 3/0279 424/45 |
| 2025/0213777 A1 * | 7/2025 | Rucinski | A61M 35/003 |

FOREIGN PATENT DOCUMENTS

| | | | | |
|---|---|---|---|---|
| JP | 2021520442 A * | 8/2021 | C11D 3/222 |

* cited by examiner

*Primary Examiner* — Guy K Townsend
(74) *Attorney, Agent, or Firm* — Hogan Lovells US LLP

(57) ABSTRACT

Novel, inexpensive, and highly effective methods and devices for convenient and effective wound irrigation are described herein. Methods and devices disclosed herein utilize a synergistic combination of two or more antiseptic agents to reduce contact time, enhance antimicrobial effects, and reduce the likelihood of allergy and other side effects from the antiseptic agents in subjects. In one embodiment, devices include a discharge means for a reservoir housing containing irrigation solution wherein the discharge means has one or more specifically designed nozzles through which a sufficient volume of the irrigation solution can pass at an appropriate pressure.

19 Claims, 3 Drawing Sheets

DETAIL C
SCALE 4 : 1

SECTION B-B
Scale 1 : 1

DEVICES AND METHODS FOR DELIVERING SYNERGISTIC ACTIVE AGENTS TO TARGET SITES

BACKGROUND OF THE INVENTION

One of the great challenges in the health care profession is delivering drugs and other therapeutic agents to the site(s) where their activity is needed. There are many therapeutic agents whose usefulness is compromised because current methods of delivery and administration do not result in optimal presentation of the agent to the site(s) where its activity would be most beneficial.

There is a wide variety of options for administering therapeutic agents to a patient. Each route of administration poses unique challenges. These challenges include formulating the active agent in a physiologically-acceptable carrier, directing the agent to the appropriate site, delivering a concentration and amount of active agent that is effective and not toxic, and avoiding degradation of the agent such as that which occurs when an agent is administered systemically and is exposed to enzymes, the immune system and various metabolic processes.

One particularly challenging environment for delivering active ingredients is to wound sites (e.g., surgical sites, and other tissue openings). These sites often require the administration of active ingredients of a nature and at a concentration that is difficult, if not impossible, to achieve utilizing systemic routes, such as oral and intravenous administration. Direct administration of an active ingredient is often desirable, yet such direct administration using conventional techniques faces formidable challenges in terms of delivering active agents to the specific tissues and cells where the beneficial activities are most needed. In this regard, it should be noted that conventional methods of wound irrigation have not typically been combined with contemporaneous drug delivery.

In the management and treatment of a wound there are three primary objectives: (1) prevention of infection, (2) preservation and/or restoration of function, and (3) preservation and/or restoration of cosmetic appearance. The most important of these objectives is the prevention of infection. Success in the prevention of infection directly affects the healing process and the degree to which function and cosmetic appearance can be preserved and/or restored. However, heretofore, wound irrigation has not been directly combined with the administration of drugs (e.g., a synergistic combination of two or more antiseptic agents) that can reduce infection or otherwise promote healing.

It is known that the number of bacteria present in a wound is a critical determinant of whether a wound becomes infected. Experimental evidence suggests that a critical level of bacteria is approximately $10^5$ organisms per gram of tissue. Below this level, wounds typically heal; at levels greater than $10^5$ bacteria per gram of tissue, wounds often become infected. All traumatic wounds are contaminated by the time the wound is presented to a medical care facility for treatment (Dire, Daniel I. [1990]"A comparison of Wound Irrigation Solutions Used in the Emergency Department," *Annals of Emergency Medicine* 19(6):704-708). Dirty wounds, or those that have not been treated within six hours, are likely to be contaminated with bacteria at levels that are higher than the critical level. Reducing the number of bacteria in and around the wound is critical for avoiding infection and expediting wound healing.

Methicillin-resistant *Staphylococcus aureus* (MRSA) infection is caused by *Staphylococcus aureus* bacteria-often called "staph." Decades ago, strains of staph emerged in hospitals that were resistant to the broad-spectrum antibiotics commonly used to treat them. These antibiotics include methicillin and other more common antibiotics such as oxacillin, penicillin, and amoxicillin. Dubbed methicillin-resistant *Staphylococcus aureus* (MRSA), it was one of the first germs to be resistant to all but the most powerful antibiotics.

Staph bacteria are generally harmless unless they enter the body through a cut or other wound. In older adults and people who are ill or have weakened immune systems, ordinary staph infections can cause serious illness. Staph infections, including MRSA, occur most frequently among persons in hospitals and healthcare facilities, such as nursing homes and dialysis centers, who have weakened immune systems.

In the 1990s, a type of MRSA began appearing in the wider community. Today, that form of staph, known as community-associated MRSA, or CA-MRSA, is responsible for many serious skin and soft tissue infections and for a serious form of pneumonia. When not treated properly, MRSA infection can be fatal.

MRSA infections are spreading rapidly in the United States and worldwide. According to the Center for Disease Control and Prevention (CDC), the proportion of infections that are antimicrobial resistant has been growing. In 1974, MRSA infections accounted for two percent of the total number of staph infections; in 1995 it was 22%; and in 2004 it was nearly 63%. Additionally, recent research has suggested that 30-50% of the population carries MRSA colonies on their bodies all the time, helping to facilitate the spread of infection.

Although MRSA has traditionally been seen as a hospital-associated infection, there has also been an epidemic of CA-MRSA in the United States. MRSA infections in the community are usually manifested as skin infections, such as pimples and boils. These CA-MRSA infections can occur in otherwise healthy people, and commonly occur among athletes who share equipment or personal items including towels and razors. In fact, from 2000 to present, there have been several reported outbreaks of CA-MRSA affecting high school athletic teams. This epidemic among athletes is aided by the fact that MRSA grows very rapidly in warm, moist areas, such as gyms and gym locker rooms. Common cuts and abrasions such as those frequently associated with football and baseball now pose significant threats due to the possibility of a MRSA infection.

Vancomycin is one of the few antibiotics still effective against hospital strains of MRSA infection, although vancomycin is no longer effective in every case. Several antibacterial agents continue to work against CA-MRSA, but CA-MRSA is a rapidly evolving bacterium, and it may only be a matter of time before it, too, becomes resistant to most antibiotics.

Different procedures of wound management have been developed to help decrease the level of bacteria present in a wound, e.g., reduce the incidence of infection. The cleansing of a wound and the site surrounding the wound to remove blood clots, debris, dirt, or other foreign materials that can introduce contaminants, including pathogenic microorganisms, is critical in reducing levels of bacteria, fungi, viruses, and protozoa in and around the wound. There are numerous wound cleansing procedures presently used by healthcare professionals such as debridement, excision, and irrigation. See, for example, Sinkinson, Craig Alan, ed. (1989) "Maximizing A Wound's Potential For Healing," *Emergency Medicine Reports* 10(11): 83-89; Lammers, Richard L.

(1991) "Soft Tissue Procedures: Principles of Wound Management," in *Clinical Procedures in Emergency Medicine, Roberts and Hedges, eds.*, 2nd Ed., W.B. Saunders Company, pp. 515-521; Cracroft, Davis (1987) "Minor Lacerations and Abrasions," *Emergency Medicine: A Comprehensive Review*, Kravis and Warner, eds., 2nd cd., Aspen Publishing Co., pp. 107-110; and Mulliken, John B. (1984) "Management of Wounds," in *Emergency Medicine*, May ed., John Wiley & Sons, pp. 283-286.

Irrigation is the most commonly used procedure for cleansing of open contaminated wounds. Irrigation involves the application of fluids to wounds to remove loose devitalized tissue, microbial inoculum (e.g., bacterial inoculum, fungal inoculum, viral inoculum, protozoal inoculum), blood clots, loose debris, and foreign bodies proximate to and within the depths of the wound. Two critical components of any effective wound irrigation method and/or device are: (1) the application of an adequate volume of sterile irrigation solution to the wound, and (2) the use of sufficient pressure applied in an effective dispersal pattern in the delivery of the solution to effectively remove contaminants. Regarding volume, the amount of irrigation solution required will depend upon the type of wound and the level of contamination. Injuries which can introduce a high amount of bacteria into a wound (such as puncture wounds and bites) may require 1 liter or more of irrigation solution.

U.S. Pat. No. 5,071,104 describes a wound irrigation apparatus and process for cleansing wounds which includes a pressure bladder, e.g., a blood pressure cuff, disposed proximate a reservoir holding a cleaning solution. The device in the '104 patent also includes a flexible tubular conduit for transmitting the solution from the reservoir to a single nozzle. The conduit and reservoir form a two-part system which is time consuming to set up, inconvenient to use, and costly.

U.S. Pat. No. 5,133,701 describes a disposable pressurized wound irrigation device which has a pressurized chamber for providing a force upon the reservoir such that a single liquid stream of cleansing solution is expelled from the device at a constant pressure. A propellant is used in evacuating the cleanser contents of the device. This invention requires a propellant and involves a relatively elaborate manufacturing and filling process which is labor intensive and requires specialized machinery. This device is also inconvenient to use and costly.

More recently, an advantageous wound irrigation system has been developed whereby a dispersed stream of irrigation fluid is easily and effectively applied to wounds. This system is described at, for example, U.S. Pat. Nos. 5,830,197 and 6,468,253 and International Patent Application publications WO 200015279A1 and WO 2002007799A2. These disclosures are incorporated herein by reference, in their entirety.

Chlorhexidine is a chemical antiseptic that combats both gram-positive and gram-negative microbes. It is bacteriostatic, hampering the growth of bacteria, and bactericidal, killing bacteria. It is often used as an active ingredient in mouthwash designed to kill dental plaque and other oral bacteria. Chlorhexidine also has non-dental applications. For example, chlorhexidine is used for general skin cleansing, as a surgical scrub, and as a pre-operative skin preparation.

Chlorhexidine is typically used in the form of acetate, gluconate, or hydrochloride. It can be deactivated by anionic compounds, including the anionic surfactants commonly used as detergents in toothpastes and mouthwashes.

BRIEF SUMMARY OF THE INVENTION

Described herein are highly effective methods and devices for efficient delivery of two or more medications or other active ingredients to a target site in a patient. Methods for irrigating a wound are described herein. Methods can include the step of providing a sterile wound irrigation solution in a wound irrigation device. Wound irrigation devices can contain a reservoir housing and a discharge means that directs a pressurized stream of a wound irrigation solution when a reservoir housing is pressurized. Methods can include the step of directing the discharge means and the reservoir housing to discharge a wound irrigation solution towards a wound. Methods can further include the step of discharging a stream of a wound irrigation solution from a reservoir housing and through a discharge means directed at a wound.

The wound irrigation solution can have any volume. An amount of wound irrigation solution applied to the wound can be any amount, such as about 10 mL to about 1000 mL of wound irrigation solution. The wound irrigation solution can have any acidity, such as between pH 5.5 and pH 7.0.

The wound irrigation solution can comprise a mixture (e.g., a synergistic combination) of antiseptic agents in solution. A wound irrigation solution can contain a combination of sterile water, a chlorhexidine, and lauroyl arginate ethyl ester (e.g., lauroyl arginate ethyl ester free base, or a pharmaceutically acceptable salt of lauroyl arginate ethyl ester). The concentration of chlorhexidine in the wound irrigation solution can be between about 100 μg/mL to about 5 mg/mL. The concentration of chlorhexidine can be about 200 μg/mL to about 1 mg/mL or about 100 μg/mL to about 500 μg/mL. The concentration of chlorhexidine can be about 500 μg/mL.

The chlorhexidine can be any pharmaceutically acceptable salt of chlorhexidine, such as chlorhexidine gluconate or the like. The concentration of lauroyl arginate ethyl ester (e.g., lauroyl arginate ethyl ester free base, or a pharmaceutically acceptable salt of lauroyl arginate ethyl ester) in the wound irrigation solution can be between about 1 μg/mL to about 200 μg/mL. For example, the concentration of lauroyl arginate ethyl ester (e.g., lauroyl arginate ethyl ester free base, or a pharmaceutically acceptable salt of lauroyl arginate ethyl ester) in the wound irrigation solution can be between about 2 μg/mL to about 100 μg/mL. The concentration of lauroyl arginate ethyl ester (e.g., lauroyl arginate ethyl ester free base, or a pharmaceutically acceptable salt of lauroyl arginate ethyl ester) in the wound irrigation solution can be between about 2 μg/mL to about 15 μg/mL or about 10 μg/mL to about 50 μg/mL. The concentration of the lauroyl arginate ethyl ester (e.g., lauroyl arginate ethyl ester free base, or a pharmaceutically acceptable salt of lauroyl arginate ethyl ester) can be about 7.5 μg/mL or about 30 μg/mL. The lauroyl arginate ethyl ester (e.g., lauroyl arginate ethyl ester free base, or a pharmaceutically acceptable salt of lauroyl arginate ethyl ester) can be any pharmaceutically acceptable salt or a free base, such as lauroyl arginate ethyl ester free base.

Methods described herein can reduce the amount of irrigation time required to reduce a microbial burden (e.g., a fungal burden, a bacterial burden, a viral burden) of a wound (e.g., reduce the time compared to another, alternative method for wound irrigation). The amount of irrigation time required can be any duration of time, such as 1 hour, 45 minutes, 30 minutes, 15 minutes, 10 minutes, 5 minutes, or 1 minute. For example, the irrigation time can be 15 minutes. The amount of time to reduce the microbial burden by any amount, such as 100-fold, can be reduced by practicing the method compared to practicing an analogous method using an alternative irrigation solution. The alternative irrigation solution can be saline (e.g., 0.9% w/w saline without an antiseptic agent). The alternative irrigation solution can be a solution containing chlorhexidine in the same concentration as wound irrigation solutions described herein, but without an additional antiseptic agent (e.g., without a lauroyl arginate ethyl ester (e.g., lauroyl arginate ethyl ester free base, or a pharmaceutically acceptable salt of lauroyl arginate ethyl ester)). The alternative irrigation solution can be a solution containing lauroyl arginate ethyl ester (e.g., lauroyl arginate ethyl ester free base, or a pharmaceutically acceptable salt of lauroyl arginate ethyl ester) in the same concentration as wound irrigation solutions described herein, but without an additional antiseptic agent (e.g., without chlorhexidine). The amount of time required to reduce a bacterial burden by methods described herein compared to an analogous method with an alternative irrigation solution can be reduced by about 50%.

The irrigation solutions of methods and devices described herein can contain a combination of a chlorhexidine and lauroyl arginate ethyl ester (e.g., lauroyl arginate ethyl ester free base, or a pharmaceutically acceptable salt of lauroyl arginate ethyl ester) that is synergistically microbiocidal or microbiostatic for any microorganism (e.g., a fungus, a bacterium). The microorganism can be any described herein, including but not limited to *Candida* species, *E. coli, Staphylococcus species, Ralstonia species, Pseudomonas* species, or a combination of any of the foregoing. The microorganism can be *E. coli, P. aeruginosa*, or a combination of *E. coli* and *P. aeruginosa.*

Methods described herein can be used to kill any microorganism (e.g., any microorganism described herein). Methods can be used to kill *Candida* species, *E. coli, Staphylococcus species, Ralstonia species, Pseudomonas* species, or combinations of any of the foregoing. Methods can be used to kill *C. albicans, E. coli*, methicillin-resistant *Staphylococcus aureus* (MRSA), *Staphylococcus aureus, Staphylococcus epidermidis, Ralstonia pickettii, P. aeruginosa*, or a combination thereof.

Methods described herein can be used to irrigate (e.g., treat) any type of wound. The type of wound can be a cut, a scrape, a surgical wound, a puncture, or an abrasion. The wound can be on any subject (e.g., any animal, any mammal). The wound can be on a human, such as a human skin wound.

DETAILED DESCRIPTION OF THE INVENTION

Figure 1:
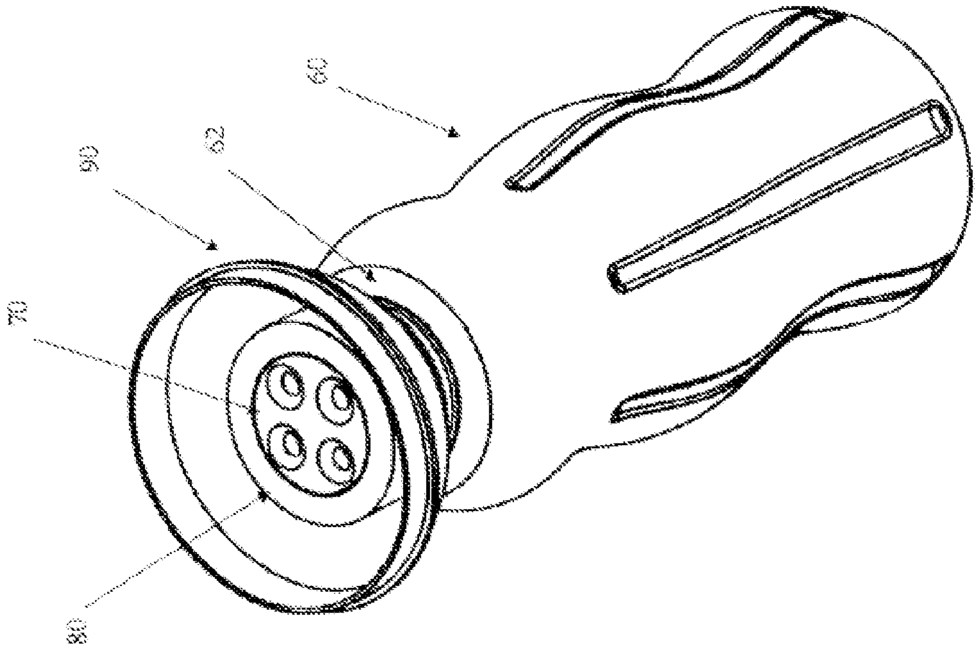
FIG. 1 shows one embodiment of the device described herein.

Described herein are novel, convenient, inexpensive, and effective drug delivery devices that comprise, in some embodiments, a reservoir housing and a discharge means having a plurality of nozzles for delivering an active agent to a target site. This disclosure also provides methods of use for drug delivery devices described herein.

The devices and methods described herein can make it possible to conveniently and easily apply one or more streams of fluid containing for example, a medicinal agent to, for example, a wound, with the stream having an appropriate volume, pressure, and dispersal pattern.

Devices and methods for irrigating a wound described herein can contain or use an irrigation solution that comprises a chlorhexidine (e.g., chlorhexidine gluconate) and lauroyl arginate ethyl ester (e.g., lauroyl arginate ethyl ester free base, or a pharmaceutically acceptable salt of lauroyl arginate ethyl ester). The chlorhexidine and lauroyl arginate ethyl ester can be at concentrations to achieve a synergistic antimicrobial (e.g., microbiostatic, microbiocidal) effect on particular microorganisms (e.g., bacterium, fungus, virus, protozoan, any microorganism described herein).

Without wishing to be bound by any one particular mechanism or theory, it is believed that by reducing the contact time of the antiseptic agents (e.g., chlorhexidine gluconate and lauroyl arginate ethyl ester) with the skin or exposed tissue of a subject (e.g., human, mammal, animal), potential hypersensitivity and allergic side effects of the antiseptic agent(s) can be reduced or eliminated. Wound irrigation solutions used in methods and devices described herein are able to reduce the contact time with the subject before rinsing with a solution that does not contain an antiseptic agent (e.g., does not contain lauroyl arginate ethyl ester and a chlorhexidine), while maintaining (or expanding the spectrum through synergistic effects) microbial killing, bacteriostatic, or fungistatic capabilities. The inventors discovered that wound irrigation solutions described herein, comprising a mixture of two or more antiseptic agents (e.g., a chlorhexidine and lauroyl arginate ethyl ester) at an effective concentration, advantageously reduce the required contact time (e.g., irrigation time) of the antiseptic agent for a desired antiseptic effect and can further increase the spectrum of antimicrobial (e.g., antibacterial, antifungal) activity when compared to single antiseptic agent wound irrigation solutions. It was also discovered that chlorhexidine and lauroyl arginate ethyl ester display a selective synergy against particular microorganisms (e.g., bacteria, fungi, viruses, protozoa, *E. coli, P. aeruginosa*) that commonly infect patients through wounds (e.g., surgical wounds, abrasions, lacerations, puncture wounds, cuts, scrapes). This is despite the fact that many antiseptic agents, for example cationic antiseptic agents (e.g., chlorhexidine and lauroyl arginate ethyl ester), were previously believed to share the same mechanism of action (e.g., binding to microbial cell walls and proteins, compromising cell wall integrity). See F. P. Deus, A. Ouanounou, Chlorhexidine in Dentistry: Pharmacology, Uses, and Adverse Effects. Int. Dent. J. (2022) 72(3), 269-277. This synergy between antiseptic agents advantageously allows for a lower concentration of antiseptic agent(s) present in the wound irrigation solution compared to single antiseptic wound irrigation solutions, further decreasing the risk of potential hypersensitivity and allergic side effects of an antiseptic agent.

This disclosure relates to methods for irrigating a wound. Methods described herein can include the step of providing a sterile wound irrigation solution in a wound irrigation device comprising a reservoir housing. The wound irrigation device in methods described herein can contain a discharge means that directs a pressurized stream of the wound irrigation solution when the reservoir housing is pressurized. The wound irrigation solution can contain sterile water and two or more antiseptic agents (e.g., two or more cationic antiseptic agents). The wound irrigation solution can contain sterile water, a chlorhexidine (e.g., chlorhexidine gluconate) and a lauroyl arginate ethyl ester (e.g., free base lauroyl arginate ethyl ester, a pharmaceutically acceptable salt of lauroyl arginate ethyl ester). The concentration of chlorhexidine can be between about 100 μg/mL to about 5 mg/mL. The concentration of lauroyl arginate ethyl ester or a pharmaceutically acceptable salt thereof can be between 1 μg/mL to about 200 μg/mL. Methods can include the step of directing the discharge means and the reservoir housing so as to discharge a wound irrigation solution towards a wound. Methods can include the step of discharging a stream of a wound irrigation solution from a reservoir housing and through a discharge means directed at the wound. In some embodiments, the wound irrigation solution consists of sterile water, a chlorhexidine, and lauroyl arginate ethyl ester or a pharmaceutically acceptable salt thereof. In some embodiments, the method for irrigating a wound contains the steps of (a) providing a sterile wound irrigation solution in a wound irrigation device comprising a reservoir housing, wherein the wound irrigation device comprises a discharge means that directs a pressurized stream of the wound irrigation solution when the reservoir housing is pressurized, and wherein the wound irrigation solution comprises sterile water, a chlorhexidine at a concentration that is between about 100 μg/mL to about 5 mg/mL, and lauroyl arginate ethyl ester or a pharmaceutically acceptable salt thereof at a concentration that is between about 1 μg/mL to about 200 μg/mL;

(b) directing the discharge means and the reservoir housing so as to discharge the wound irrigation solution toward the wound; and (c) discharging a stream of the wound irrigation solution from the reservoir housing and through the discharge means directed at the wound.

Definitions

All publications (e.g., scientific journal articles, patent publications, and the like) cited in this disclosure are incorporated by reference in their entirety. To the extent the material incorporated by reference contradicts or is inconsistent with this specification, the specification will supersede any such material. The citation of any references herein is not an admission that such references are prior art to the present disclosure. Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the term "active agents" refers to compounds or other entities that perform a therapeutic and/or diagnostic function. This function may be direct, such as promoting tissue repair or killing pathogenic microorganisms (e.g., bacteria, fungi, viruses, protozoa), or may be indirect by eliciting a physiological response that ultimately results in the desired beneficial result. For example, the active agent can be an antiseptic agent that is microbiostatic (e.g., inhibits the proliferation of a microorganism such as a bacterium, fungus, virus, protozoa, or the like) and/or microbiocidal (e.g., kills a microorganism such as a bacterium, fungus, virus, protozoa, or the like).

As used herein, the term "pharmaceutically acceptable salt" refers to a salt of the compound prepared with relatively nontoxic acids or bases, depending on the particular substituents found on the respective compound. When compounds of the present disclosure contain relatively acidic functionalities, base addition salts can be obtained by contacting the neutral form of such compounds with a sufficient amount of the desired base, either neat or in a suitable solvent (e.g., an inert solvent). Examples of pharmaceutically acceptable base addition salts include sodium, potassium, calcium, ammonium, organic amino, magnesium salt, or a similar salt. When compounds relating to the present disclosure contain relatively basic functionalities, acid addition salts can be obtained by contacting the neutral form of such compounds with a sufficient amount of the desired acid, either neat or in a suitable solvent (e.g., an inert solvent). Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic (acetate), propionic, isobutyric, maleic, malonic, benzoic, succinic, suberic, fumaric, lactic, mandelic, pamoic (pamoate), phthalic, benzenesulfonic, p-toluenesulfonic, citric, tartaric, methanesulfonic (mesylate), and the like. Also included are salts of amino acids such as arginate and the like, and salts of organic acids like glucuronic or galacturonic acids and the like. Certain compounds of the present disclosure can contain both basic and acidic functionalities that allow the compounds to be converted into either base or acid addition salts. These salts may be prepared by methods known to those skilled in the art. Other pharmaceutically acceptable salts known to those of skill in the art are suitable for pharmaceutical compositions relating to the present disclosure.

Throughout this disclosure, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

The articles "a" and "an" are used herein to refer to one or more than one (e.g., to at least one) of the grammatical object of the article. By way of example, "an element" means one element or more than one element.

The term "about" when referring to a measurable value such as an amount, a temporal duration, and the like, is meant to encompass variations of ±20% or less, or in some instances ±15% or less, or in some instances ±10% or less, or in some instances ±5% or less, or in some instances ±1% or less, or in some instances ±0.1% or less, from the specified value, as such variations are appropriate.

The phrase "and/or" as used herein should be understood to mean "either or both" of the elements so conjoined, e.g., elements that are conjunctively present in some cases and disjunctively present in other cases. Multiple elements listed with "and/or" should be construed in the same fashion, e.g., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The term "effective amount" or a "therapeutically effective amount" as used herein refers to an amount of a compound, or a pharmaceutical composition, described herein which is sufficient to achieve a desired result under the conditions of administration. A skilled clinician can determine appropriate dosing based on a variety of considerations including the severity of the disease, the subject's age, weight, general health, and other considerations. A pharmaceutical composition disclosed herein may be administered to provide an amount of about 0.01 mg to about 1800 mg of a therapeutic agent.

The term "pharmaceutically acceptable excipient" as used herein refers to a non-toxic material that may be formulated with a compound disclosed herein to provide a pharmaceutical composition. Preferably, the pharmaceutically acceptable excipient is inert and does not interfere with the pharmacological activity of a compound which it is formulated with. Pharmaceutically acceptable excipients useful in the manufacture of the pharmaceutical compositions disclosed herein are any of those well known in the art, and include without limitation, diluents, dispersing agents, granulating agents, surface active agents, emulsifiers, disintegrating agents, binding agents, preservatives, buffering agents, lubricating agents, ion exchangers, salts, electrolytes, waxes, and/or oils. For example, a pharmaceutically acceptable excipient may be alumina, aluminum stearate, lecithin, a serum protein (e.g., human serum albumin), a phosphate, glycine, sorbic acid, potassium sorbate, a glyceride mixture (e.g., saturated vegetable fatty acids), water, protamine sulfate, disodium hydrogen phosphate, potassium hydrogen phosphate, sodium chloride, a zinc salt, colloidal silica, magnesium trisilicate, polyvinyl pyrrolidone, cellulose or a derivative thereof, polyethylene glycol or a derivative thereof (e.g., PEG-300), sodium carboxymethylcellulose, a polyacrylate, a polyethylene-polyoxypropylene-block polymer, wool fat, a cyclodextrin (e.g., CAPTISOL®), dimethylacetamide (DMA), a polysorbate (e.g., a TWEEN®, e.g., TWEEN-20®), ethylenediaminetetraacetic acid (EDTA) or a salt thereof, and any combination thereof.

The term "subject" as used herein refers to any animal, such as any mammal, including but not limited to, humans, non-human primates, rodents, dogs, and the like. Non-human primates include chimpanzees, cynomolgus monkeys, spider monkeys, and macaques (e.g., Rhesus). Rodents include mice, rats, woodchucks, ferrets, rabbits, and hamsters. Domestic and game animals include cows, horses, pigs, deer, bison, buffalo, feline species (e.g., domestic cat), canine species (e.g., dog, fox, wolf), avian species, and fish. In some embodiments, the subject is a mammal (e.g., a human, a rat, or a mouse). The subject can be male or female. The subject may be of any age, including an elderly human subject (e.g., 65 years or older), a human subject that is not elderly (e.g., less than 65 years old), or a human pediatric subject (e.g., 18 years old or less). In preferred aspects, the subject is a human.

As used herein, the terms "treat," "treatment," "treating," or grammatically related terms, refer to a method of reducing the effects of a disease or disorder. As is readily appreciated in the art, full eradication of the disease, disorder, or symptoms thereof is preferred but not a requirement for treatment. Desirable effects of treatment include, but are not limited to, preventing occurrence or recurrence of the disease or disorder, alleviation of symptoms, diminishment of any direct or indirect pathological consequences of the disease or disorder, or other improvement of any sign, symptom, or consequence of the disease or disorder, such as prolonged survival, less morbidity, and/or a lessening of side effects.

Throughout this disclosure, various embodiments can be presented in a range format (e.g., from X-Y). It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 5, from 1 to 4, from 1 to 3, from 2 to 6, from 2 to 4, from 3 to 6, etc., as well as individual numbers within that range, e.g., 1, 2, 2.8, 3, 3.6, 4, 5, 5.4, and 6. As another example, a range such as 95-99% includes 95%, 96%, 97%, 98%, or 99% and all subranges such as 96-99%, 96-98%, 96-97%, 97-99%, 97-98%, etc. This applies regardless of the breadth of the range.

Wound Irrigation Solutions

Wound irrigation solutions described herein contain two or more antiseptic agents. Without wishing to be bound by any one particular mechanism of action or theory, it is believed that wound irrigation solutions containing a chlorhexidine and lauroyl arginate ethyl ester have a synergistic antimicrobial (e.g., microbiostatic, fungistatic, bacteriostatic, microbiocidal, fungicidal, bactericidal) effect and/or reduce the contact time (e.g., irrigation time) required for an antimicrobial effect against particular microorganisms (e.g., a microorganism described herein). It is further believed that, through reduction of the contact time (e.g., irrigation time) required to obtain a desired antimicrobial effect in methods described herein, the likelihood of a subject experiencing an adverse reaction (e.g., sensitivity, allergic response, pain) to one or more antiseptics present in the wound irrigation solution can be reduced.

The wound irrigation solution can contain a synergistic combination of two or more antiseptic agents in solution. The wound irrigation solution can be a solution an aqueous solution, including but not limited to, water or salt solution (e.g., saline). The wound irrigation solution can be an emulsion, a biphasic mixture, or a triphasic mixture (e.g., a solution of water with a non-miscible cosolvent). The wound irrigation solution can be non-sterile, sterile filtered or terminally sterilized (e.g., can contain sterile water). In some embodiments, the irrigation solution is a sterile water (not saline) solution containing 0.05% or less (or even less than 0.04% or even less than 0.03%) of chlorhexidine that is applied to a wound in the skin of a human. Preferably the wound is then rinsed within five minutes (e.g., more preferably within 1-3 minutes) with a sterile saline, water, or other liquid that does not contain an antiseptic agent (e.g., does not contain a chlorhexidine, does not contain lauroyl arginate ethyl ester).

In some embodiments, the synergistic mixture of antiseptics used according to the methods and devices described herein includes a chlorhexidine and has the chemical structure according to Formula (I):

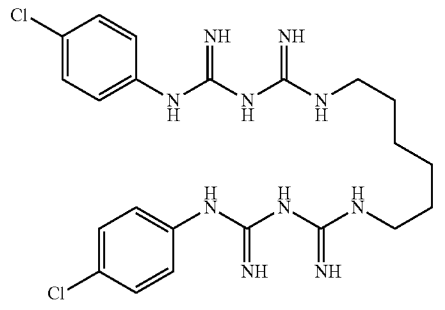 [SMILES: N=C(NCCCCCCNC(=N)NC(=N)Nc1ccc(Cl)cc1)NC(=N)Nc1ccc(Cl)cc1]

Chlorhexidine

Systematic (IUPAC) Name: 1-[amino-[6-[amino-[amino-(4-chlorophenyl)amino-methylidene]amino-methylidene]aminohexylimino]methyl]imino-N-(4-chlorophenyl)-methanediamine;

Chemical Data

Formula: $C_{22}H_{30}Cl_2N_{10}$

Mol. Weight: 505.446 g/mol

The chlorhexidine as used in methods and devices described herein can be in the form of a salt, such as any pharmaceutically acceptable salt of chlorhexidine. The anion (e.g., the counter anion) of the chlorhexidine salt can be any anion including, but not limited to, any carboxylate (e.g., formate, acetate, propionate, isopropionate, butyrate, isobutyrate, maleate, malonate, benzoate, succinate, suberate, fumarate, lactate, mandelate, pamoate, phthalate, citrate, tartrate, gluconate, and the like) or halide (e.g., fluoride, chloride, bromide, iodide). In some embodiments, the synergistic mixture of antiseptics used according to the methods and devices described herein includes a chlorhexidine acetate salt (e.g., chlorhexidine diacetate). In some embodiments, the synergistic mixture of antiseptics used according to the methods and devices described herein includes a chlorhexidine gluconate salt (e.g., a chlorhexidine gluconate salt, chlorhexidine digluconate). In some embodiments, the synergistic mixture of antiseptics used according to the methods and devices described herein includes chlorhexidine digluconate and has chemical structure according to Formula (II):

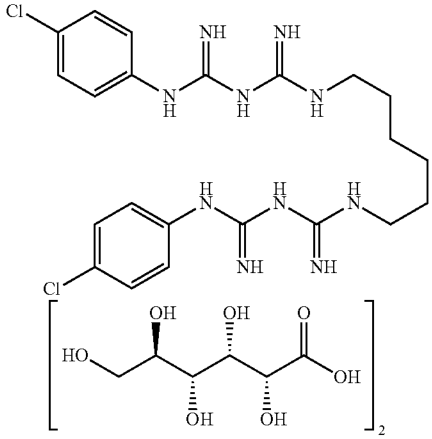

Chlorhexidine Digluconate

Systematic (IUPAC) Name: 1-[amino-[6-[amino-[amino-(4-chlorophenyl)amino-methylidene]amino-methylidene]aminohexylimino]methyl]imino-N-(4-chlorophenyl)-methanediamine; (2R,3S,4R,5R)-2,3,4,5,6-pentahydroxyhexanoic acid.

Chemical Data

Formula: $C_{34}H_{54}Cl_2N_{10}O_{14}$

Mol. Weight: 897.762 g/mol

In some embodiments, the synergistic mixture of antiseptics used according to the methods and devices described herein includes lauroyl arginate ethyl ester and has a chemical structure of Formula (III):

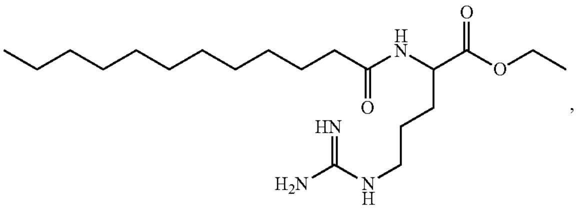 [SMILES: CCCCCCCCCCCC(=O)NC(CCCNC(=N)N)C(=O)OCC]

,

The lauroyl arginate ethyl ester can be in the form of any pharmaceutically acceptable salt (e.g., ethyl lauroyl arginate hydrochloride). The counter anion ($X^-$) of the lauroyl arginate ethyl ester of Formula (IV):

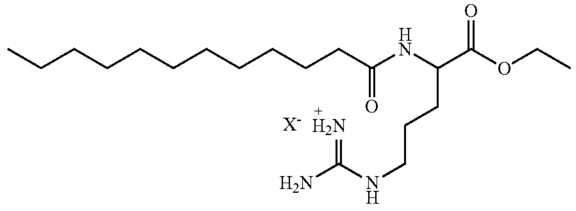

can be any anion including, but not limited to, a halide, sulfate, mesylate, maleate, citrate, tartrate, phosphate, acetate, or gluconate. The counter anion ($X^-$) can be any halogen anion including, but not limited to, fluoride ($F^-$), chloride ($Cl^-$), bromide ($Br^-$), or iodide ($I^-$).

The lauroyl arginate ethyl ester t can be a mixture of lauroyl arginate ethyl ester free base and/or pharmaceutically acceptable salts thereof. The mixture of lauroyl arginate ethyl ester can be a mixture of lauroyl arginate ethyl ester containing differing counter ions (e.g., $X^-$, counter anions, a mixture containing hydroiodide and hydrochloride lauroyl arginate ethyl ester salts). The mixture of lauroyl arginate ethyl ester and pharmaceutically acceptable salts thereof can contain a number of differing lauroyl arginate ethyl ester pharmaceutically acceptable salts that is 2, 3, 4, 5, 6, 7, 8, 9, 10, 11, 12, 13, 14, 15, 16, 17, 18, 19, or 20. The number of differing lauroyl arginate ethyl ester pharmaceutically acceptable salts in a mixture can range from 2 to 3, 2 to 4, 2 to 5, 3 to 4, 3 to 5, or 4 to 5.

In some embodiments, the lauroyl arginate ethyl ester or pharmaceutically acceptable salt thereof is free base lauroyl arginate ethyl ester. In some embodiments, the lauroyl arginate ethyl ester salt is ethyl lauroyl arginate hydrochloride Any amount of chlorhexidine (e.g., chlorhexidine gluconate) can be applied to a wound in methods described herein. The amount of chlorhexidine applied to a wound can be between about 1 mg to about 750 mg, about 1 mg to about 700 mg, about 1 mg to about 650 mg, about 1 mg to about 600 mg, about 1 mg to about 550 mg, about 1 mg to about 500 mg, about 1 mg to about 450 mg, about 1 mg to about 400 mg, about 1 mg to about 350 mg, about 1 mg to about 300 mg, about 1 mg to about 250 mg, about 1 mg to about 200 mg, about 1 mg to about 150 mg, about 1 mg to about 100 mg, about 1 mg to about 75 mg, about 1 mg to about 50 mg, about 1 mg to about 25 mg, about 5 mg to about 750 mg, about 10 mg to about 750 mg, about 15 mg to about 750 mg, about 20 mg to about 750 mg, about 25 mg to about 750 mg, about 30 mg to about 750 mg, about 35 mg to about 750 mg, about 40 mg to about 750 mg, about 45 mg to about 750 mg, about 50 mg to about 750 mg, about 55 mg to about 750 mg, about 60 mg to about 750 mg, about 65 mg to about 750 mg, about 70 mg to about 750 mg, about 75 mg to about 750 mg, about 80 mg to about 750 mg, about 85 mg to about 750 mg, about 90 mg to about 750 mg, about 95 mg to about 750 mg, about 100 mg to about 750 mg, about 110 mg to about 750 mg, about 120 mg to about 750 mg, about 140 mg to about 750 mg, about 160 mg to about 750 mg, about 180 mg to about 750 mg, about 200 mg to about 750 mg, about 240 mg to about 750 mg, about 280 mg to about 750 mg, about 300 mg to about 750 mg, about 350 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, about 700 mg to about 750 mg, about 10 mg to about 30 mg, about 5 mg to about 40 mg, about 5 mg to about 50 mg, about 5 mg to about 60 mg, about 5 mg to about 70 mg, or about 5 mg to about 80 mg. In some embodiments, about 15 to about 25 mg of chlorhexidine gluconate is applied to a wound. In some embodiments, the wound is an abrasion or laceration, and the wound irrigation solution is applied prior to repair/closure.

Any amount of lauroyl arginate ethyl ester (e.g., a pharmaceutically acceptable salt of lauroyl arginate ethyl ester) can be applied to a wound in methods described herein. The amount of lauroyl arginate ethyl ester applied to a wound can be between about 50 μg to about 150 μg, about 60 μg to about 150 μg, about 70 μg to about 150 μg, about 80 μg to about 150 μg, about 90 μg to about 150 μg, about 100 μg to about 150 μg, about 110 μg to about 150 μg, about 120 μg to about 150 μg, about 130 μg to about 150 μg, about 140 μg to about 150 μg, about 125 μg to about 750 μg, about 150 μg to about 750 μg, about 175 μg to about 750 μg, about 200 μg to about 750 μg, about 250 μg to about 750 μg, about 300 μg to about 750 μg, about 350 μg to about 750 μg, about 400 μg to about 750 μg, about 450 μg to about 750 μg, about 500 μg to about 750 μg, about 550 μg to about 750 μg, about 600 μg to about 750 μg, about 650 μg to about 750 μg, about 700 μg to about 750 μg, about 125 μg to about 1500 μg, about 150 μg to about 1500 μg, about 175 μg to about 1500 μg, about 200 μg to about 1500 μg, about 250 μg to about 1500 μg, about 300 μg to about 1500 μg, about 350 μg to about 1500 μg, about 400 μg to about 1500 μg, about 450 μg to about 1500 μg, about 500 μg to about 1500 μg, about 550 μg to about 1500 μg, about 600 μg to about 1500 μg, about 650 μg to about 1500 μg, about 700 μg to about 1500 μg, about 1 mg to about 750 mg, about 1 mg to about 700 mg, about 1 mg to about 650 mg, about 1 mg to about 600 mg, about 1 mg to about 550 mg, about 1 mg to about 500 mg, about 1 mg to about 450 mg, about 1 mg to about 400 mg, about 1 mg to about 350 mg, about 1 mg to about 300 mg, about 1 mg to about 250 mg, about 1 mg to about 200 mg, about 1 mg to about 150 mg, about 1 mg to about 100 mg, about 1 mg to about 75 mg, about 1 mg to about 50 mg, about 1 mg to about 25 mg, about 5 mg to about 750 mg, about 10 mg to about 750 mg, about 15 mg to about 750 mg, about 20 mg to about 750 mg, about 25 mg to about 750 mg, about 30 mg to about 750 mg, about 35 mg to about 750 mg, about 40 mg to about 750 mg, about 45 mg to about 750 mg, about 50 mg to about 750 mg, about 55 mg to about 750 mg, about 60 mg to about 750 mg, about 65 mg to about 750 mg, about 70 mg to about 750 mg, about 75 mg to about 750 mg, about 80 mg to about 750 mg, about 85 mg to about 750 mg, about 90 mg to about 750 mg, about 95 mg to about 750 mg, about 100 mg to about 750 mg, about 110 mg to about 750 mg, about 120 mg to about 750 mg, about 140 mg to about 750 mg, about 160 mg to about 750 mg, about 180 mg to about 750 mg, about 200 mg to about 750 mg, about 240 mg to about 750 mg, about 280 mg to about 750 mg, about 300 mg to about 750 mg, about 350 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, about 700 mg to about 750 mg, about 10 mg to about 30 mg, about 5 mg to about 40 mg, about 5 mg to about 50 mg, about 5 mg to about 60 mg, about 5 mg to about 70 mg, or about 5 mg to about 80 mg. In some embodiments, about 15 mg to about 25 mg of lauroyl arginate ethyl ester is applied to a wound.

The pH of the wound irrigation solution can be neutral or slightly acidic. The pH can be between about 3.0 to about 7.0, about 3.5 to about 7.0, about 4.0 to about 7.0, about 4.5 to about 7.0, about 5.0 to about 7.0, about 6.0 to about 7.0, about 5.0 to about 6.5, or about 5.0 to about 6.0. In some embodiments, the pH is 5.0 to 7.5. In some embodiments, the pH is 5.5 to 7.0. In some embodiments, the chlorhexidine is applied without a sudsing agent.

Application of the wound irrigation solutions described herein reduce the number of microorganisms at the wound when compared to an untreated wound or a wound treated with an irrigation solution that contains saline and does not contain an antiseptic agent (e.g., a chlorhexidine, lauroyl arginate ethyl ester, or a combination thereof). In some embodiments, the application of the wound irrigation solution in methods and devices described herein results in a reduction in the number of microorganisms (e.g., bacteria, fungi, protozoan, virus) at the wound when compared to either an untreated wound or a wound irrigation with saline that does not contain chlorhexidine and lauroyl arginate ethyl ester. In some embodiments, the application of the wound irrigation solution in methods and devices described herein results in a reduction in the number of microorganisms (e.g., bacteria, fungi, protozoan, virus) at the wound when compared to either an untreated wound or a wound irrigation with saline that does not contain a synergistic combination of two or more antiseptic agents (e.g., a combination of lauroyl arginate ethyl ester and chlorhexidine). In some embodiments, the application of the wound irrigation solution in methods and devices described herein results in a reduction in the number of bacteria at the wound when compared to either an untreated wound or a wound irrigation with saline that does not contain chlorhexidine. In some embodiments, the application of the wound irrigation solution in methods and devices described herein results in a reduction in the number of bacteria at the wound when compared to either an untreated wound or a wound irrigation with saline that does not contain lauroyl arginate ethyl ester (e.g., does not contain a pharmaceutically acceptable salt of lauroyl arginate ethyl ester).

Advantageously, the wound irrigation solutions of the methods and devices described herein can be effective in combating infection, even when organic materials (including blood, desired tissue, and/or dirt and debris) are present.

In addition to killing bacteria, the formulations of the used in the methods and devices described herein can also "depathogenize" (e.g., reduce the pathogenicity of) certain bacteria or fungi including, for example, *E. coli* and *Klebsiella aerogenes*, making these bacteria or fungi less able to cause infection. Formulations used in methods and devices described herein can reduce the pathogenicity of any bacteria or fungi, such as the bacteria and fungi described herein.

The drug delivery methods described herein can be used in conjunction with the delivery of an active agent by many of the routes set forth in Table 1. In some embodiments, the delivery route for wound irrigation solutions of devices and methods described herein is buccal, conjunctival, cutaneous, dental, intra-abdominal, intralesional, intraocular, intrathoracic (during surgery), irrigation, nasal, ophthalmic, periodontal, rectal, soft tissue, subcutaneous, topical, and vaginal.

The drug delivery devices and methods described herein can be utilized by trained medical technicians; however, because of the simplicity and convenience of the devices and methods described herein, they can be used to greatly enhance the effectiveness of drug delivery regardless of the training level of the operator performing the irrigation.

Delivering Active Agents

Examples of agents that can be administered to a subject (e.g., a human, a human patient) in accordance with the methods and devices described herein include, but are not limited to, bacterial agents, anti-viral agents, fungicidal agents, chemotherapy agents, topical antiseptics, anesthetic agents, oxygenated fluids and/or agents, antibiotics, diagnostic agents, homeopathic agents, and over the counter medications/agents. In some embodiments, the wound irrigation solution administered to a subject comprises sterile water, a chlorhexidine and lauroyl arginate ethyl ester or a pharmaceutically acceptable salt thereof.

The target sites to which an active ingredient can be administered according to the methods and devices described herein include, but are not limited to, wounds, the eyes, and surgical sites. The surgical sites may include, for example, joint replacements, abdominal surgery, and oral/periodontal surgery sites. In each case, the ability to deliver the active agent to a specific site, at an appropriate dosage, at a carefully controlled pressure, is unique and highly advantageous.

The solution (e.g., solvent) that carries the active agent can be, for example, water, saline, or a balanced salt solution. The solution that carries the active agent can be sterile (e.g., a sterile aqueous solution of active agent). The device can be sterilized by known sterilization techniques, including boiling, autoclaving, gas sterilization, sterile filtration, and the like, either separately or together with the reservoir housing.

Buffered Ringer's solution or commercially available balanced salt solution (e.g., Tis-U-Sol® (Baxter International Inc.) or PhysioSol™ (ICU Medical, Inc.)) are physiologically compatible and are commonly used in wound irrigation procedures.

The antiseptic agents most commonly used in wound care at present include:

Povidone-iodine solution (Betadine preparation)-iodine added to the carrier polyvinylpyrrolidone (PVP), a water-soluble organic complex; this combination is called an iodophor. Standard solutions of Betadine preparation are 10 percent.

Povidone-iodine surgical scrub (Betadine scrub)—the iodophor PVP-J and an anionic detergent (pH 4.5).

pHisoHex (Sanofi S. A.)—an emulsion of an anionic detergent, entsulfon, lanolin cholesterols, petrolatum, and hexachlorophene (pH 5.5).

Hi-Bi-clens (Mölnlycke Health Care)-chlorhexidine gluconate plus a sudsing base (pH 5.1 to 6.5).

Tincture of green soap-potassium oleate, isopropanol, potassium coconut oil, soap.

Dakin's solution 0.2 percent solution hypochlorite solution.

Hydrogen peroxide—an oxidizing agent.

Nonionic surfactants-Pluronic F-68 (e.g., Shur-Clens® (ConvaTec Inc.)) and Poloxamer-188 (e.g., PharmaClens® (Ecolab Inc.))-agents that have no antimicrobial activity (pH 7.1).

The use of chlorhexidine is particularly advantageous because it is broad spectrum, binds to the skin (to provide residual activity), works rapidly and, when used according to the methods described herein, is non-toxic.

Chlorhexidine is a chemical antiseptic, which can be used to combat both gram-positive and gram-negative microbes. It is both bacteriostatic and bactericidal. Various species of bacteria are involved in the pathogenesis of wound infection and/or secondarily cellulitis. At times, these infections can result in disfigurement, loss of extremities, prolonged convalesces, and/or death. The therapeutic effects of wound irrigation solutions used in the devices and methods described herein are to combat microbes typically involved in the pathology of these infections by their antiseptic properties and those associated with the irrigation process itself. Controlling the microbial load in wounds is a vital factor in minimizing infection and thus decreasing and/or preventing disease.

Spectrum of Activity

Chlorhexidine is active against aerobic and anaerobic gram-positive and gram-negative bacteria. The drug also has some activity against *Chlamydia trachomatis*, certain fungi, and certain viruses.

As the use of broad-spectrum antibiotics has increased in prevalence, many emerging bacteria and fungal species of concern are evolving resistance to conventional antibiotic treatments. Emerging bacteria of concern include, but are not limited to, *Burkholderia* species (e.g., *Burkholderia mallei, Burkholderia pseudomallei, Burkholderia glumae*), *Bordetella* species (e.g., *Bordetella pertussis, Bordetella parapertussis, Bordetella bronchispetica*), *Campylobacter* species (e.g., drug-resistant *Campylobacter* spp., *C. jejuni, C. concisus, C. lari*), *Enterobacterales* species (e.g., extended-spectrum beta-lactamase-producing *Enterobacterales* spp., carbapenem-resistant *Enterobacterales* spp., *E. coli, Klebsiella pneumoniae, K. oxytoca, Kluyvera* spp., *Proteus mirabilis, Serratia marcescens*, Drug-resistant *Shigella* spp., *Shigella boydii, Shigella dysenteriae, Shigella flexneri, Shigella sonnei, Enterobacter aerogenes, Enterobacter cloacae, Enterobacter sakasakii, Citrobacter koseri, Citrobacter braakii, Citrobacter freundii, Salmonella enterica, Salmonella bongori, Morganella morganii, Providencia rettgeri, Raoultella planticola*), *Acinetobacter* species (e.g., carbapenem-resistant *Acinetobacter* spp., *A. baumannii, A. haemolyticus, A. nosocomialis, A. pittii, A. calcoaceticus, A. ursingii, A. variabilis, A. soli, A. seifertii*), *Clostridioides difficile, Mycoplasma* species (e.g., *Mycoplasma pneumoniae, Mycoplasma genitalium, Mycoplasma amphoriforme, Mycoplasma buccale, Mycoplasma fermentans, Mycoplasma hominis*), *Neisseria* species (e.g., drug-resistant *Neisseria gonorrhoeae*), *Enterococci* species (e.g., vancomycin-resistant *Enterococci* spp., *E. faecalis, E. faecium, E. duran, E. avium, E. gallinarum, E. casseliflavus, E. hirae, E. mundtii, E. raffinosus*), *Pseudomonas* species (e.g., drug-resistant *Pseudomonas* spp., *P. aeruginosa*), *Ralstonia* species (e.g., *Ralstonia pickettii, Ralstonia insidiosa, Ralstonia mannitolilytica, Ralstonia pseudosolanacearum, Ralstonia solanacearum, Ralstonia syzygii*), *Streptococcus* species (e.g., drug-resistant *Streptococcus* spp., *Streptococcus pneumoniae, Streptococcus pyogenes, Streptococcus sanguinis, Streptococcus mutans, Streptococcus agalactiae*, erythromycin-resistant group A *Streptococcus* spp., Clindamycin-resistant group B *Streptococcus* spp.) and combinations thereof. Emerging fungi of concern include, but are not limited to, *Candida* species (e.g., drug-resistant *Candida* spp., *Candida albicans, Candida glabrata, Candida krusei, Candida parapsilosis, Candida tropicalis, Candida auris*), *Aspergillus* species (e.g., azole-resistant *Aspergillus* spp., *Aspergillus fumigatus, Aspergillus flavus, Aspergillus hiratsukae, Aspergillus niger, Aspergillus terreus*), *Fusarium* species (e.g., *Fusarium oxysporum, Fusarium solani*), *Mucor* species (e.g., *Mucor circinelloides*), *Rhizopus* species (e.g., *Rhizopus arrhizus*), and combinations thereof.

The methods and devices disclosed herein can be used to inhibit or kill any microbial organism (e.g., any bacteria, fungi, protozoa, virus). The methods and devices disclosed herein can use a wound irrigation solution comprising two or more antiseptic agents (e.g., a chlorhexidine and lauroyl arginate ethyl ester or a pharmaceutically acceptable salt thereof) to inhibit or kill any bacteria including, but not limited to, *Acinetobacter* spp., *Bordetella* spp., *Burkholderia* spp., *Campylobacter* spp., *Clostridioides difficile, Cutibacterium* spp. (e.g., *Cutibacterium acnes, Cutibacterium* avidum, *Cutibacterium granulosum, Cutibacterium modestum, Cutibacterium namnetense, Cutibacterium porci*), *Enterobacterales* spp., *Enterococci* spp., *Lactobacillus* spp. (*L. rhamnosus, L. acidophilus, L. casei, L. fermentum, L. paracasei, L. corneformis*), *Mycoplasma* spp., *Neisseria* spp., *Pseudomonas* spp., *Ralstonia* spp., *Staphylococcus* spp., *Streptococcus* spp., or combinations thereof. The methods and devices disclosed herein can be used to inhibit or kill any bacteria described herein. The methods and devices disclosed herein can be used to inhibit or kill any fungi including, but not limited to, *Candida* spp., *Aspergillus* spp., *Fusarium* spp., *Mucor* spp., *Rhizopus* spp., or combinations thereof. The methods and devices disclosed herein can be used to inhibit or kill any fungi described herein. In some embodiments, the methods described herein are used to kill *Candida* species, *E. coli, Staphylococcus species, Ralstonia species, Pseudomonas* species, or a combination thereof. In some embodiments, the methods described herein are used to kill *Cutibacterium* spp. (e.g., *Cutibacterium acnes*). In some embodiments, the methods described herein are used to kill *Lactobacillus* spp. (*L. rhamnosus*). In some embodiments, the methods described herein are used to kill *C. albicans, E. coli*, methicillin-resistant *Staphylococcus aureus, Staphylococcus aureus, Staphylococcus epidermidis, Ralstonia pickettii, P. aeruginosa*, or a combination thereof. In some embodiments, the methods described herein are used to kill *C. albicans*. In some embodiments, the methods described herein are used to kill *E. coli*. In some embodiments, the methods described herein are used to kill *Staphylococcus aureus* (e.g., methicillin-resistant *Staphylococcus aureus*, MRSA). In some embodiments, the methods described herein are used to kill *Staphylococcus epidermidis*. In some embodiments, the methods described herein are used to kill *Ralstonia pickettii*. In some embodiments, the methods described herein are used to kill *P. aeruginosa*. In some embodiments, the methods described herein are used to kill *Candida* sp. In some embodiments, the methods described herein are used to kill *Escherichia* sp. In some embodiments, the methods described herein are used to kill *Staphylococcus* sp. In some embodiments, the methods described herein are used to kill *Ralstonia* sp. In some embodiments, the methods described herein are used to kill *Pseudomonas* sp.

Aerobic Bacteria

Chlorhexidine is highly active against a variety of gram-positive aerobic bacteria, including *Streptococcus mutans, S. pyogenes* (group A 3-hemolytic streptococci), *S. salivarius*, and *S. sanguis*. Chlorhexidine is active against *Staphylococcus aureus, S. epidermidis, S. haemolyticus, S. haominis*, and *S. simulans*. Chlorhexidine is active against both oxacillin-resistant (ORSA) and oxacillin-susceptible staphylococci (also known as methicillin-resistant [MRSA] or methicillin-susceptible staphylococci).

Chlorhexidine is active against *Enterococcus*, including *E. faecalis* and *E. faecium*, and is active against both vancomycin-susceptible and vancomycin-resistant strains.

Anaerobic Bacteria

Chlorhexidine is active against some anaerobic bacteria. It is active against some strains of *Bacteroides, Propionibacterium, Clostridium difficile*, and *Selenomonas*, but is less active against *Veillonella.*

Fungi

Chlorhexidine has some activity against *Candida albicans, C. dubliniensis, C. glabrata* (formerly *Torulopsis glabrata*), *C. guillermondii, C. kefyr* (formerly *C. pseudotropicalis*), *C. krusei, C. lusitaniae*, and *C. tropicalis* (formerly *C. parapsilosis*). Chlorhexidine also has some activity against dermatophytes, including *Epidermophyton floccosum, Microsporum gypseum, M. canis*, and *Trichophyton mentagrophytes.*

Viruses

Chlorhexidine has antiviral activity against viruses that have a lipid component in their outer coat or have an outer envelope such as cytomegalovirus (CMV), human immunodeficiency virus (HIV), herpes simplex virus types 1 (HSV-1) and 2 (HSV-2), influenza virus, parainfluenza virus, coronavirus (e.g., SARS, SARS-CoV-2) and variola virus (smallpox virus). For example, see Y. H. Huang and J. T. Huang, Use of chlorhexidine to eradicate oropharyngeal SARS-CoV-2 in COVID-19 patients, J. Med. Virol. 2021; 93 (7), 4370-4373.

Methods and Formulations

Advantageously, because the methods described herein can be used to accurately and efficiently deliver a combination of two or more antiseptic agents (e.g., a synergistic combination of two or more antiseptic agents) to a target site in a subject (e.g., a human, a human patient), it is possible, in certain embodiments, to utilize reduced concentrations of one or more antiseptic agent. In some embodiments, a low concentration solution of chlorhexidine can be used to effectively reduce infections and/or microbial burden (e.g., fungal burden, bacterial burden, viral burden, protozoal burden) at, for example, a wound, surgical site, or other tissue opening.

Wound irrigation solutions of methods and devices described herein can contain any concentration of an antiseptic agent. The concentration of the antiseptic agent can be between about 5 μg/mL to about 1 mg/mL, about 6 μg/mL to about 1 mg/mL, about 7 μg/mL to about 1 mg/mL, about 8 μg/mL to about 1 mg/mL, about 9 μg/mL to about 1 mg/mL, about 10 μg/mL to about 1 mg/mL, about 12 μg/mL to about 1 mg/mL, about 14 μg/mL to about 1 mg/mL, about 16 μg/mL to about 1 mg/mL, about 18 μg/mL to about 1 mg/mL, about 20 μg/mL to about 1 mg/mL, about 24 μg/mL to about 1 mg/mL, about 28 μg/mL to about 1 mg/mL, about 30 μg/mL to about 1 mg/mL, about 35 μg/mL to about 1 mg/mL, about 40 μg/mL to about 1 mg/mL, about 45 μg/mL to about 1 mg/mL, about 50 μg/mL to about 1 mg/mL, about 55 μg/mL to about 1 mg/mL, about 60 μg/mL to about 1 mg/mL, about 65 μg/mL to about 1 mg/mL, about 70 μg/mL to about 1 mg/mL, about 75 μg/mL to about 1 mg/mL, about 80 μg/mL to about 1 mg/mL, about 85 μg/mL to about 1 mg/mL, about 90 μg/mL to about 1 mg/mL, about 95 μg/mL to about 1 mg/mL, about 100 μg/mL to about 1 mg/mL, about 120 μg/mL to about 1 mg/mL, about 140 μg/mL to about 1 mg/mL, about 160 μg/mL to about 1 mg/mL, about 180 μg/mL to about 1 mg/mL, about 200 μg/mL to about 1 mg/mL, about 250 μg/mL to about 1 mg/mL, about 300 μg/mL to about 1 mg/mL, about 350 μg/mL to about 1 mg/mL, about 400 μg/mL to about 1 mg/mL, about 450 μg/mL to about 1 mg/mL, about 500 μg/mL to about 1 mg/mL, about 550 μg/mL to about 1 mg/mL, about 600 μg/mL to about 1 mg/mL, about 650 μg/mL to about 1 mg/mL, about 700 μg/mL to about 1 mg/mL, about 750 μg/mL to about 1 mg/mL, about 800 μg/mL to about 1 mg/mL, about 850 μg/mL to about 1 mg/mL, about 900 μg/mL to about 1 mg/mL, about 950 μg/mL to about 1 mg/mL, about 5 μg/mL to about 950 μg/mL, about 5 μg/mL to about 900 μg/mL, about 5 μg/mL to about 850 μg/mL, about 5 μg/mL to about 800 μg/mL, about 5 μg/mL to about 750 μg/mL, about 5 μg/mL to about 700 μg/mL, about 5 μg/mL to about 650 μg/mL, about 5 μg/mL to about 600 μg/mL, about 5 μg/mL to about 550 μg/mL, about 5 μg/mL to about 500 μg/mL, about 5 μg/mL to about 450 μg/mL, about 5 μg/mL to about 400 μg/mL, about 5 μg/mL to about 375 μg/mL, about 5 μg/mL to about 350 μg/mL, about 5 μg/mL to about 325 μg/mL, about 5 μg/mL to about 300 μg/mL, about 5 μg/mL to about 275 μg/mL, about 5 μg/mL to about 250 μg/mL, about 5 μg/mL to about 225 μg/mL, about 5 μg/mL to about 200 μg/mL, about 5 μg/mL to about 175 μg/mL, about 5 μg/mL to about 150 μg/mL, about 5 μg/mL to about 125 μg/mL, about 5 μg/mL to about 100 μg/mL, about 5 μg/mL to about 75 μg/mL, about 5 μg/mL to about 50 μg/mL, about 5 μg/mL to about 25 μg/mL, about 5 μg/mL to about 20 μg/mL, about 5 μg/mL to about 15 μg/mL, about 5 μg/mL to about 10 μg/mL, about 10 μg/mL to about 500 μg/mL, about 15 μg/mL to about 500 μg/mL, about 20 μg/mL to about 500 μg/mL, about 25 μg/mL to about 500 μg/mL, about 30 μg/mL to about 500 μg/mL, about 35 μg/mL to about 500 μg/mL, about 40 μg/mL to about 500 μg/mL, about 45 μg/mL to about 500 μg/mL, about 50 μg/mL to about 500 μg/mL, about 55 μg/mL to about 500 μg/mL, about 60 μg/mL to about 500 μg/mL, about 65 μg/mL to about 500 μg/mL, about 70 μg/mL to about 500 μg/mL, about 75 μg/mL to about 500 μg/mL, about 80 μg/mL to about 500 μg/mL, about 85 μg/mL to about 500 μg/mL, about 90 μg/mL to about 500 μg/mL, about 100 μg/mL to about 500 μg/mL, about 110 μg/mL to about 500 μg/mL, about 120 μg/mL to about 500 μg/mL, about 130 μg/mL to about 500 μg/mL, about 140 μg/mL to about 500 μg/mL, about 150 μg/mL to about 500 μg/mL, about 160 μg/mL to about 500 μg/mL, about 170 μg/mL to about 500 μg/mL, about 180 μg/mL to about 500 μg/mL, about 190 μg/mL to about 500 μg/mL, about 200 μg/mL to about 500 μg/mL, about 240 μg/mL to about 500 μg/mL, about 280 μg/mL to about 500 μg/mL, about 300 μg/mL to about 500 μg/mL, about 350 μg/mL to about 500 μg/mL, about 400 μg/mL to about 500 μg/mL, about 450 μg/mL to about 500 μg/mL, about 10 μg/mL to about 450 μg/mL, about 10 μg/mL to about 400 μg/mL, about 10 μg/mL to about 375 μg/mL, about 10 μg/mL to about 350 μg/mL, about 10 μg/mL to about 325 μg/mL, about 10 μg/mL to about 300 μg/mL, about 10 μg/mL to about 275 μg/mL, about 10 μg/mL to about 250 μg/mL, about 10 μg/mL to about 225 μg/mL, about 10 μg/mL to about 200 μg/mL, about 10 μg/mL to about 175 μg/mL, about 10 μg/mL to about 150 μg/mL, about 10 μg/mL to about 125 μg/mL, about 10 μg/mL to about 100 μg/mL, about 10 μg/mL to about 90 μg/mL, about 10 μg/mL to about 80 μg/mL, about 10 μg/mL to about 70 μg/mL, about 10 μg/mL to about 60 μg/mL, about 10 μg/mL to about 50 μg/mL, about 10 μg/mL to about 45 μg/mL, about 10 μg/mL to about 40 μg/mL, about 10 μg/mL to about 35 μg/mL, about 10 μg/mL to about 30 μg/mL, about 10 μg/mL to about 25 μg/mL, about 10 μg/mL to about 20 μg/mL, about 10 μg/mL to about 15 μg/mL, about 30 μg/mL to about 200 μg/mL, about 35 μg/mL to about 200 μg/mL, about 40 μg/mL to about 200 μg/mL, about 45 μg/mL to about 200 μg/mL, about 50 μg/mL to about 200 μg/mL, about 55 μg/mL to about 200 μg/mL, about 60 μg/mL to about 200 μg/mL, about 65 μg/mL to about 200 μg/mL, about 70 μg/mL to about 200 μg/mL, about 75 μg/mL to about 200 μg/mL, about 80 μg/mL to about 200 μg/mL, about 85 μg/mL to about 200 μg/mL, about 90 μg/mL to about 200 μg/mL, about 95 μg/mL to about 200 μg/mL, about 100 μg/mL to about 200 μg/mL, about 110 μg/mL to about 200 μg/mL, about 120 μg/mL to about 200 μg/mL, about 130 μg/mL to about 200 μg/mL, about 140 μg/mL to about 200 μg/mL, about 150 μg/mL to about 200 μg/mL, about 160 μg/mL to about 200 μg/mL, about 170 μg/mL to about 200 μg/mL, about 180 μg/mL to about 200 μg/mL, about 190 μg/mL to about 200 μg/mL, about 30 μg/mL to about 190 μg/mL, about 30 μg/mL to about 180 μg/mL, about 30 μg/mL to about 170 μg/mL, about 30 μg/mL to about 160 μg/mL, about 30 μg/mL to about 150 μg/mL, about 30 μg/mL to about 140 μg/mL, about 30 μg/mL to about 130 μg/mL, about 30 μg/mL to about 120 μg/mL, about 30 μg/mL to about 110 μg/mL, about 30 μg/mL to about 100 μg/mL, about 30 μg/mL to about 95 μg/mL, about 30 μg/mL to about 90 μg/mL, about 30 μg/mL to about 85 μg/mL, about 30 μg/mL to about 80 μg/mL, about 30 μg/mL to about 75 μg/mL, about 30 μg/mL to about 70 μg/mL, about 30 μg/mL to about 65 μg/mL, about 30 μg/mL to about 60 μg/mL, about 30 μg/mL to about 55 μg/mL, about 30 μg/mL to about 50 μg/mL, about 30 μg/mL to about 45 μg/mL, about 30 μg/mL to about 40 μg/mL, about 60 μg/mL to about 180 μg/mL, about 65 μg/mL to about 180 μg/mL, about 70 μg/mL to about 180 μg/mL, about 75 μg/mL to about 180 μg/mL, about 80 μg/mL to about 180 μg/mL, about 85 μg/mL to about 180 μg/mL, about 90 μg/mL to about 180 μg/mL, about 95 μg/mL to about 180 μg/mL, about 100 μg/mL to about 180 μg/mL, about 105 μg/mL to about 180 μg/mL, about 110 μg/mL to about 180 μg/mL, about 115 μg/mL to about 180 μg/mL, about 120 μg/mL to about 180 μg/mL, about 125 μg/mL to about 180 μg/mL, about 130 μg/mL to about 180 μg/mL, about 135 μg/mL to about 180 μg/mL, about 140 μg/mL to about 180 μg/mL, about 145 μg/mL to about 180 μg/mL, about 150 μg/mL to about 180 μg/mL, about 155 μg/mL to about 180 μg/mL, about 160 μg/mL to about 180 μg/mL, about 165 μg/mL to about 180 μg/mL, about 170 μg/mL to about 180 μg/mL, about 175 μg/mL to about 180 μg/mL, about 60 μg/mL to about 175 μg/mL, about 60 μg/mL to about 170 μg/mL, about 60 μg/mL to about 165 μg/mL, about 60 μg/mL to about 160 μg/mL, about 60 μg/mL to about 155 μg/mL, about 60 μg/mL to about 150 μg/mL, about 60 μg/mL to about 145 μg/mL, about 60 μg/mL to about 140 μg/mL, about 60 μg/mL to about 135 μg/mL, about 60 μg/mL to about 130 μg/mL, about 60 μg/mL to about 125 μg/mL, about 60 μg/mL to about 120 μg/mL, about 60 μg/mL to about 115 μg/mL, about 60 μg/mL to about 110 μg/mL, about 60 μg/mL to about 105 μg/mL, about 60 μg/mL to about 100 μg/mL, about 60 μg/mL to about 95 μg/mL, about 60 μg/mL to about 90 μg/mL, about 60 μg/mL to about 85 μg/mL, about 60 μg/mL to about 80 μg/mL, about 60 μg/mL to about 75 μg/mL, about 60 μg/mL to about 70 μg/mL, about 60 μg/mL to about 65 μg/mL, about 35 μg/mL to about 90 μg/mL, about 40 μg/mL to about 90 μg/mL, about 45 μg/mL to about 90 μg/mL, about 50 μg/mL to about 90 μg/mL, about 55 μg/mL to about 90 μg/mL, about 60 μg/mL to about 90 μg/mL, about 65 μg/mL to about 90 μg/mL, about 70 μg/mL to about 90 μg/mL, about 75 μg/mL to about 90 μg/mL, about 80 μg/mL to about 90 μg/mL, or about 85 μg/mL to about 90 μg/mL. The concentration of the antiseptic agent can be about 5 μg/mL, about 10 μg/mL, about 15 μg/mL, about 20 μg/mL, about 25 μg/mL, about 30 μg/mL, about 35 μg/mL, about 40 μg/mL, about 45 μg/mL, about 50 μg/mL, about 55 μg/mL, about 60 μg/mL, about 65 μg/mL, about 70 μg/mL, about 75 μg/mL, about 80 μg/mL, about 85 μg/mL, about 90 μg/mL, about 95 μg/mL, about 100 μg/mL, about 110 μg/mL, about 120 μg/mL, about 130 μg/mL, about 140 μg/mL, about 150 μg/mL, about 160 μg/mL, about 170 μg/mL, about 180 μg/mL, about 190 μg/mL, about 200 μg/mL, about 220 μg/mL, about 240 μg/mL, about 260 μg/mL, about 280 μg/mL, about 300 μg/mL, about 330 μg/mL, about 360 μg/mL, about 390 μg/mL, about 400 μg/mL, about 440 μg/mL, about 480 μg/mL, about 500 μg/mL, about 550 μg/mL, about 600 μg/mL, about 650 μg/mL, about 700 μg/mL, about 750 μg/mL, about 800 μg/mL, about 850 μg/mL, about 900 μg/mL, about 950 μg/mL, or about 1 mg/mL.

Wound irrigation solutions used in the methods and devices described herein can contain any concentration of a chlorhexidine (e.g., chlorhexidine gluconate). The concentration of the chlorhexidine can be between about 50 μg/mL to about 100 mg/mL, about 50 μg/mL to about 90 mg/mL, about 50 μg/mL to about 80 mg/mL, about 50 μg/mL to about 70 mg/mL, about 50 μg/mL to about 60 mg/mL, about 50 μg/mL to about 50 mg/mL, about 50 μg/mL to about 40 mg/mL, about 50 μg/mL to about 30 mg/mL, about 50 μg/mL to about 20 mg/mL, about 50 μg/mL to about 100 mg/mL, about 100 μg/mL to about 100 mg/mL, about 150 μg/mL to about 100 mg/mL, about 200 μg/mL to about 100 mg/mL, about 300 μg/mL to about 100 mg/mL, about 400 μg/mL to about 100 mg/mL, about 500 μg/mL to about 100 mg/mL, about 50 μg/mL to about 10 mg/mL, about 50 μg/mL to about 5 mg/mL, about 50 μg/mL to about 2.5 mg/mL, about 50 μg/mL to about 2 mg/mL, about 50 μg/mL to about 1 mg/mL, about 50 μg/mL to about 750 μg/mL, about 50 μg/mL to about 500 μg/mL, about 50 μg/mL to about 400 μg/mL, about 50 μg/mL to about 300 μg/mL, about 50 μg/mL to about 200 μg/mL, about 50 μg/mL to about 100 μg/mL, about 50 μg/mL to about 90 μg/mL, about 50 μg/mL to about 80 μg/mL, about 50 μg/mL to about 60 μg/mL, about 60 μg/mL to about 10 mg/mL, about 80 μg/mL to about 10 mg/mL, about 100 μg/mL to about 10 mg/mL, about 150 μg/mL to about 10 mg/mL, about 200 μg/mL to about 10 mg/mL, about 250 μg/mL to about 10 mg/mL, about 300 μg/mL to about 10 mg/mL, about 350 μg/mL to about 10 mg/mL, about 400 μg/mL to about 10 mg/mL, about 450 μg/mL to about 10 mg/mL, about 500 μg/mL to about 10 mg/mL, about 550 μg/mL to about 10 mg/mL, about 600 μg/mL to about 10 mg/mL, about 650 μg/mL to about 10 mg/mL, about 700 μg/mL to about 10 mg/mL, about 750 μg/mL to about 10 mg/mL, about 800 μg/mL to about 10 mg/mL, about 900 μg/mL to about 10 mg/mL, about 1 mg/mL to about 10 mg/mL, about 2 mg/mL to about 10 mg/mL, about 3 mg/mL to about 10 mg/mL, about 4 mg/mL to about 10 mg/mL, about 5 mg/mL to about 10 mg/mL, about 6 mg/mL to about 10 mg/mL, about 7 mg/mL to about 10 mg/mL, about 8 mg/mL to about 10 mg/mL, about 9 mg/mL to about 10 mg/mL, about 100 μg/mL to about 5 mg/mL, about 150 μg/mL to about 5 mg/mL, about 200 μg/mL to about 5 mg/mL, about 250 μg/mL to about 5 mg/mL, about 300 μg/mL to about 5 mg/mL, about 350 μg/mL to about 5 mg/mL, about 400 μg/mL to about 5 mg/mL, about 450 μg/mL to about 5 mg/mL, about 500 μg/mL to about 5 mg/mL, about 550 μg/mL to about 5 mg/mL, about 600 μg/mL to about 5 mg/mL, about 650 μg/mL to about 5 mg/mL, about 700 μg/mL to about 5 mg/mL, about 750 μg/mL to about 5 mg/mL, about 800 μg/mL to about 5 mg/mL, about 850 μg/mL to about 5 mg/mL, about 900 μg/mL to about 5 mg/mL, about 950 μg/mL to about 5 mg/mL, about 1 mg/mL to about 5 mg/mL, about 2 mg/mL to about 5 mg/mL, about 3 mg/mL to about 5 mg/mL, about 4 mg/mL to about 5 mg/mL, about 100 μg/mL to about 4 mg/mL, about 100 μg/mL to about 3 mg/mL, about 100 μg/mL to about 2 mg/mL, about 100 μg/mL to about 1 mg/mL, about 100 μg/mL to about 950 μg/mL, about 100 μg/mL to about 900 μg/mL, about 100 μg/mL to about 850 μg/mL, about 100 μg/mL to about 800 μg/mL, about 100 μg/mL to about 750 μg/mL, about 100 μg/mL to about 700 μg/mL, about 100 μg/mL to about 650 μg/mL, about 100 μg/mL to about 600 μg/mL, about 100 μg/mL to about 550 μg/mL, about 100 μg/mL to about 500 μg/mL, about 100 μg/mL to about 450 μg/mL, about 100 μg/mL to about 400 μg/mL, about 100 μg/mL to about 350 μg/mL, about 100 μg/mL to about 300 μg/mL, about 100 μg/mL to about 250 μg/mL, about 100 μg/mL to about 200 μg/mL, about 100 μg/mL to about 175 μg/mL, about 100 μg/mL to about 150 μg/mL, about 100 μg/mL to about 125 μg/mL, about 200 μg/mL to about 1 mg/mL, 250 μg/mL to about 1 mg/mL, 300 μg/mL to about 1 mg/mL, 350 μg/mL to about 1 mg/mL, 400 μg/mL to about 1 mg/mL, 450 μg/mL to about 1 mg/mL, 500 μg/mL to about 1 mg/mL, 550 μg/mL to about 1 mg/mL, 600 μg/mL to about 1 mg/mL, 650 μg/mL to about 1 mg/mL, 700 μg/mL to about 1 mg/mL, 750 μg/mL to about 1 mg/mL, 800 μg/mL to about 1 mg/mL, 850 μg/mL to about 1 mg/mL, 900 μg/mL to about 1 mg/mL, 950 μg/mL to about 1 mg/mL, about 200 μg/mL to about 950 μg/mL, about 200 μg/mL to about 900 μg/mL, about 200 μg/mL to about 850 μg/mL, about 200 μg/mL to about 800 μg/mL, about 200 μg/mL to about 750 μg/mL, about 200 μg/mL to about 700 μg/mL, about 200 μg/mL to about 650 μg/mL, about 200 μg/mL to about 600 μg/mL, about 200 μg/mL to about 550 μg/mL, about 200 μg/mL to about 500 μg/mL, about 200 μg/mL to about 450 μg/mL, about 200 μg/mL to about 400 μg/mL, about 200 μg/mL to about 350 μg/mL, about 200 μg/mL to about 300 μg/mL, or about 200 μg/mL to about 250 μg/mL. The concentration of the chlorhexidine can be about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2 mg/mL, about 1.5 mg/mL, about 1.25 mg/mL, about 1 mg/mL, about 900 μg/mL, about 850 μg/mL, about 800 μg/mL, about 750 μg/mL, about 700 μg/mL, about 650 μg/mL, about 600 μg/mL, about 550 μg/mL, about 500 μg/mL, about 450 μg/mL, about 400 μg/mL, about 350 μg/mL, about 325 μg/mL, about 300 μg/mL, about 275 μg/mL, about 250 μg/mL, about 225 μg/mL, about 200 μg/mL, about 175 μg/mL, about 170 μg/mL, about 160 μg/mL, about 150 μg/mL, about 140 μg/mL, about 130 μg/mL, about 120 μg/mL, about 110 μg/mL, about 100 μg/mL, about 90 μg/mL, about 80 μg/mL, about 70 μg/mL, about 65 μg/mL, about 60 μg/mL, about 55 μg/mL, about 50 μg/mL, about 45 μg/mL, about 40 μg/mL, about 35 μg/mL, about 30 μg/mL, about 25 μg/mL, about 20 μg/mL, about 15 μg/mL, about 10 μg/mL, about 5 μg/mL, about 2 μg/mL, or about 1 μg/mL.

In some embodiments, the chlorhexidine concentration in the wound irrigation solution is less than 4% w/w. In some embodiments, the chlorhexidine is less than 2% w/w, or even less than 1% w/w. In one embodiment, the chlorhexidine concentration in the wound irrigation solution is 0.05% w/w. In a further embodiment, the chlorhexidine concentration in the wound irrigation solution is between 0.02% and 0.05% w/w. In some embodiments, the concentration of the chlorhexidine in the wound irrigation solution is between about 100 μg/mL to about 5 mg/mL. In some embodiments, the concentration of the chlorhexidine in the wound irrigation solution is between about 200 μg/mL to about 1 mg/mL or about 100 μg/mL to about 500 μg/mL. In some embodiments, the concentration of the chlorhexidine in the wound irrigation solution is about 500 μg/mL. Specifically exemplified herein is the use of chlorhexidine gluconate.

Wound irrigation solutions of methods and devices described herein can contain any concentration of a lauroyl arginate ethyl ester (e.g., a pharmaceutically acceptable salt of lauroyl arginate ethyl ester). The concentration of the lauroyl arginate ethyl ester can be between about 5 μg/mL to about 10 mg/mL, about 5 μg/mL to about 9 mg/mL, about 5 μg/mL to about 8 mg/mL, about 5 μg/mL to about 7 mg/mL, about 5 μg/mL to about 6 mg/mL, about 5 μg/mL to about 5 mg/mL, about 5 μg/mL to about 4 mg/mL, about 5 μg/mL to about 3 mg/mL, about 5 μg/mL to about 2 mg/mL, 10 μg/mL to about 10 mg/mL, about 20 μg/mL to about 10 mg/mL, about 30 μg/mL to about 10 mg/mL, about 40 μg/mL to about 10 mg/mL, about 50 μg/mL to about 10 mg/mL, about 60 μg/mL to about 10 mg/mL, about 0.5 μg/mL to about 1 mg/mL, about 0.6 μg/mL to about 1 mg/mL, about 0.7 μg/mL to about 1 mg/mL, about 0.8 μg/mL to about 1 mg/mL, about 0.9 μg/mL to about 1 mg/mL, about 1.0 μg/mL to about 1 mg/mL, about 1.2 μg/mL to about 1 mg/mL, about 1.4 μg/mL to about 1 mg/mL, about 1.6 μg/mL to about 1 mg/mL, about 1.8 μg/mL to about 1 mg/mL, about 2.0 μg/mL to about 1 mg/mL, about 2.4 μg/mL to about 1 mg/mL, about 2.8 μg/mL to about 1 mg/mL, about 3.0 μg/mL to about 1 mg/mL, about 3.5 μg/mL to about 1 mg/mL, about 4.0 μg/mL to about 1 mg/mL, about 4.5 μg/mL to about 1 mg/mL, about 5 μg/mL to about 1 mg/mL, about 6 μg/mL to about 1 mg/mL, about 7 μg/mL to about 1 mg/mL, about 8 μg/mL to about 1 mg/mL, about 9 μg/mL to about 1 mg/mL, about 10 μg/mL to about 1 mg/mL, about 12 μg/mL to about 1 mg/mL, about 14 μg/mL to about 1 mg/mL, about 16 μg/mL to about 1 mg/mL, about 18 μg/mL to about 1 mg/mL, about 20 μg/mL to about 1 mg/mL, about 24 μg/mL to about 1 mg/mL, about 28 μg/mL to about 1 mg/mL, about 30 μg/mL to about 1 mg/mL, about 35 μg/mL to about 1 mg/mL, about 40 μg/mL to about 1 mg/mL, about 45 μg/mL to about 1 mg/mL, about 50 μg/mL to about 1 mg/mL, about 55 μg/mL to about 1 mg/mL, about 60 μg/mL to about 1 mg/mL, about 65 μg/mL to about 1 mg/mL, about 70 μg/mL to about 1 mg/mL, about 75 μg/mL to about 1 mg/mL, about 80 μg/mL to about 1 mg/mL, about 85 μg/mL to about 1 mg/mL, about 90 μg/mL to about 1 mg/mL, about 95 μg/mL to about 1 mg/mL, about 100 μg/mL to about 1 mg/mL, about 120 μg/mL to about 1 mg/mL, about 140 μg/mL to about 1 mg/mL, about 160 μg/mL to about 1 mg/mL, about 180 μg/mL to about 1 mg/mL, about 200 μg/mL to about 1 mg/mL, about 250 μg/mL to about 1 mg/mL, about 300 μg/mL to about 1 mg/mL, about 350 μg/mL to about 1 mg/mL, about 400 μg/mL to about 1 mg/mL, about 450 μg/mL to about 1 mg/mL, about 500 μg/mL to about 1 mg/mL, about 550 μg/mL to about 1 mg/mL, about 600 μg/mL to about 1 mg/mL, about 650 μg/mL to about 1 mg/mL, about 700 μg/mL to about 1 mg/mL, about 750 μg/mL to about 1 mg/mL, about 800 μg/mL to about 1 mg/mL, about 850 μg/mL to about 1 mg/mL, about 900 μg/mL to about 1 mg/mL, about 950 μg/mL to about 1 mg/mL, about 0.5 μg/mL to about 950 μg/mL, about 0.5 μg/mL to about 900 μg/mL, about 0.5 μg/mL to about 850 μg/mL, about 0.5 μg/mL to about 800 μg/mL, about 0.5 μg/mL to about 750 μg/mL, about 0.5 μg/mL to about 700 μg/mL, about 0.5 μg/mL to about 650 μg/mL, about 0.5 μg/mL to about 600 μg/mL, about 0.5 μg/mL to about 550 μg/mL, about 0.5 μg/mL to about 500 μg/mL, about 0.5 μg/mL to about 450 μg/mL, about 0.5 μg/mL to about 400 μg/mL, about 0.5 μg/mL to about 375 μg/mL, about 0.5 μg/mL to about 350 μg/mL, about 0.5 μg/mL to about 325 μg/mL, about 0.5 μg/mL to about 300 μg/mL, about 0.5 μg/mL to about 275 μg/mL, about 0.5 μg/mL to about 250 μg/mL, about 0.5 μg/mL to about 225 μg/mL, about 0.5 μg/mL to about 200 μg/mL, about 0.5 μg/mL to about 175 μg/mL, about 0.5 μg/mL to about 150 μg/mL, about 0.5 μg/mL to about 125 μg/mL, about 0.5 μg/mL to about 100 μg/mL, about 0.5 μg/mL to about 75 μg/mL, about 0.5 μg/mL to about 50 μg/mL, about 0.5 μg/mL to about 25 μg/mL, about 0.5 μg/mL to about 20 μg/mL, about 0.5 μg/mL to about 15 μg/mL, about 0.5 μg/mL to about 10 μg/mL, about 0.5 μg/mL to about 9 μg/mL, about 0.5 μg/mL to about 8.5 μg/mL, about 0.5 μg/mL to about 8 μg/mL, about 0.5 μg/mL to about 7.5 μg/mL, about 0.5 μg/mL to about 7 μg/mL, about 0.5 μg/mL to about 6.5 μg/mL, about 0.5 μg/mL to about 6 μg/mL, about 0.5 μg/mL to about 5.5 μg/mL, about 0.5 μg/mL to about 4 μg/mL, about 0.5 μg/mL to about 3.8 μg/mL, about 0.5 μg/mL to about 3.6 μg/mL, about 0.5 μg/mL to about 3.4 μg/mL, about 0.5 μg/mL to about 3.2 μg/mL, about 0.5 μg/mL to about 3 μg/mL, about 0.5 μg/mL to about 2.8 μg/mL, about 0.5 μg/mL to about 2.6 μg/mL, about 0.5 μg/mL to about 2.4 μg/mL, about 0.5 μg/mL to about 2.2 μg/mL, about 0.5 μg/mL to about 2 μg/mL, about 0.5 μg/mL to about 1.8 μg/mL, about 0.5 μg/mL to about 1.6 μg/mL, about 0.5 μg/mL to about 1.4 μg/mL, about 0.5 μg/mL to about 1.2 μg/mL, about 0.5 μg/mL to about 1 μg/mL, about 1 μg/mL to about 200 μg/mL, about 1.2 μg/mL to about 200 μg/mL, about 1.4 μg/mL to about 200 μg/mL, about 1.8 μg/mL to about 200 μg/mL, about 2 μg/mL to about 200 μg/mL, about 2.2 μg/mL to about 200 μg/mL, about 2.4 μg/mL to about 200 μg/mL, about 2.6 μg/mL to about 200 μg/mL, about 2.8 μg/mL to about 200 μg/mL, about 3 μg/mL to about 200 μg/mL, about 3.2 μg/mL to about 200 μg/mL, about 3.4 μg/mL to about 200 μg/mL, about 3.6 μg/mL to about 200 μg/mL, about 3.8 μg/mL to about 200 μg/mL, about 4 μg/mL to about 200 μg/mL, about 4.5 μg/mL to about 200 μg/mL, about 5 μg/mL to about 200 μg/mL, about 5.5 μg/mL to about 200 μg/mL, about 6 μg/mL to about 200 μg/mL, about 6.5 μg/mL to about 200 μg/mL, about 7 μg/mL to about 200 μg/mL, about 7.5 μg/mL to about 200 μg/mL, about 8 μg/mL to about 200 μg/mL, about 8.5 μg/mL to about 200 μg/mL, about 9 μg/mL to about 200 μg/mL, about 9.5 μg/mL to about 200 μg/mL, about 10 μg/mL to about 200 μg/mL, about 15 μg/mL to about 200 μg/mL, about 20 μg/mL to about 200 μg/mL, about 25 μg/mL to about 200 μg/mL, about 30 μg/mL to about 200 μg/mL, about 35 μg/mL to about 200 μg/mL, about 40 μg/mL to about 200 μg/mL, about 45 μg/mL to about 200 μg/mL, about 50 μg/mL to about 200 μg/mL, about 55 μg/mL to about 200 μg/mL, about 60 μg/mL to about 200 μg/mL, about 65 μg/mL to about 200 μg/mL, about 70 μg/mL to about 200 μg/mL, about 75 μg/mL to about 200 μg/mL, about 80 μg/mL to about 200 μg/mL, about 85 μg/mL to about 200 μg/mL, about 90 μg/mL to about 200 μg/mL, about 100 μg/mL to about 200 μg/mL, about 110 μg/mL to about 200 μg/mL, about 120 μg/mL to about 200 μg/mL, about 130 μg/mL to about 200 μg/mL, about 140 μg/mL to about 200 μg/mL, about 150 μg/mL to about 200 μg/mL, about 160 μg/mL to about 200 μg/mL, about 170 μg/mL to about 200 μg/mL, about 180 μg/mL to about 200 μg/mL, about 190 μg/mL to about 200 μg/mL, about 1 μg/mL to about 190 μg/mL, about 1 μg/mL to about 180 μg/mL, about 1 μg/mL to about 160 μg/mL, about 10 μg/mL to about 140 μg/mL, about 1 μg/mL to about 130 μg/mL, about 1 μg/mL to about 120 μg/mL, about 1 μg/mL to about 100 μg/mL, about 1 μg/mL to about 90 μg/mL, about 1 μg/mL to about 80 μg/mL, about 1 μg/mL to about 70 μg/mL, about 1 μg/mL to about 60 μg/mL, about 10 μg/mL to about 50 μg/mL, about 1 μg/mL to about 45 μg/mL, about 1 μg/mL to about 40 μg/mL, about 1 μg/mL to about 35 μg/mL, about 1 μg/mL to about 30 μg/mL, about 10 μg/mL to about 25 μg/mL, about 1 μg/mL to about 20 μg/mL, about 1 μg/mL to about 15 μg/mL, about 1 μg/mL to about 12 μg/mL, about 1 μg/mL to about 10 μg/mL, about 1 μg/mL to about 9.5 μg/mL, about 1 μg/mL to about 9 μg/mL, about 1 μg/mL to about 8.5 μg/mL, about 1 μg/mL to about 8 μg/mL, about 1 μg/mL to about 7.5 μg/mL, about 1 μg/mL to about 7 μg/mL, about 1 μg/mL to about 6.5 μg/mL, about 1 μg/mL to about 6 μg/mL, about 1 μg/mL to about 5.5 μg/mL, about 1 μg/mL to about 5 μg/mL, about 1 μg/mL to about 4.5 μg/mL, about 1 μg/mL to about 4.25 μg/mL, about 1 μg/mL to about 4 μg/mL, about 1 μg/mL to about 3.8 μg/mL, about 1 μg/mL to about 3.6 μg/mL, about 1 μg/mL to about 3.4 μg/mL, about 1 μg/mL to about 3.2 μg/mL, about 1 μg/mL to about 3 μg/mL, about 1 μg/mL to about 2.8 μg/mL, about 1 μg/mL to about 2.6 μg/mL, about 1 μg/mL to about 2.4 μg/mL, about 1 μg/mL to about 2.2 μg/mL, about 1 μg/mL to about 2 μg/mL, about 1 μg/mL to about 1.8 μg/mL, about 1 μg/mL to about 1.6 μg/mL, about 1 μg/mL to about 1.4 μg/mL, about 1 μg/mL to about 1.2 μg/mL, about 2 μg/mL to about 100 μg/mL, about 2.2 μg/mL to about 100 μg/mL, about 2.4 μg/mL to about 100 μg/mL, about 2.6 μg/mL to about 100 μg/mL, about 2.8 μg/mL to about 100 μg/mL, about 3 μg/mL to about 100 μg/mL, about 3.2 μg/mL to about 100 μg/mL, about 3.4 μg/mL to about 100 μg/mL, about 3.6 μg/mL to about 100 μg/mL, about 3.8 μg/mL to about 100 μg/mL, about 4 μg/mL to about 100 μg/mL, about 4.5 μg/mL to about 100 μg/mL, about 5 μg/mL to about 100 μg/mL, about 5.5 μg/mL to about 100 μg/mL, about 6 μg/mL to about 100 μg/mL, about 6.5 μg/mL to about 100 μg/mL, about 7 μg/mL to about 100 μg/mL, about 7.5 μg/mL to about 100 μg/mL, about 8 μg/mL to about 100 μg/mL, about 8.5 μg/mL to about 100 μg/mL, about 9 μg/mL to about 100 μg/mL, about 9.5 μg/mL to about 100 μg/mL, about 10 μg/mL to about 100 μg/mL, about 11 μg/mL to about 100 μg/mL, about 12 μg/mL to about 100 μg/mL, about 13 μg/mL to about 100 μg/mL, about 14 μg/mL to about 100 μg/mL, about 15 μg/mL to about 100 μg/mL, about 16 μg/mL to about 100 μg/mL, about 17 μg/mL to about 100 μg/mL, about 18 μg/mL to about 100 μg/mL, about 19 μg/mL to about 100 μg/mL, about 20 μg/mL to about 100 μg/mL, about 22 μg/mL to about 100 μg/mL, about 24 μg/mL to about 100 μg/mL, about 26 μg/mL to about 100 μg/mL, about 28 μg/mL to about 100 μg/mL, about 30 μg/mL to about 100 μg/mL, about 35 μg/mL to about 100 μg/mL, about 40 μg/mL to about 100 μg/mL, about 45 μg/mL to about 100 μg/mL, about 50 μg/mL to about 100 μg/mL, about 55 μg/mL to about 100 μg/mL, about 60 μg/mL to about 100 μg/mL, about 65 μg/mL to about 100 μg/mL, about 70 μg/mL to about 100 μg/mL, about 75 μg/mL to about 100 μg/mL, about 80 μg/mL to about 100 μg/mL, about 85 μg/mL to about 100 μg/mL, about 90 μg/mL to about 100 μg/mL, about 95 μg/mL to about 100 μg/mL, about 2 μg/mL to about 95 μg/mL, about 2 μg/mL to about 90 μg/mL, about 2 μg/mL to about 85 μg/mL, about 2 μg/mL to about 80 μg/mL, about 2 μg/mL to about 75 μg/mL, about 2 μg/mL to about 70 μg/mL, about 2 μg/mL to about 65 μg/mL, about 2 μg/mL to about 60 μg/mL, about 2 μg/mL to about 55 μg/mL, about 2 μg/mL to about 50 μg/mL, about 2 μg/mL to about 45 μg/mL, about 2 μg/mL to about 40 μg/mL, about 2 μg/mL to about 35 μg/mL, about 2 μg/mL to about 30 μg/mL, about 2 μg/mL to about 28 μg/mL, about 2 μg/mL to about 26 μg/mL, about 2 μg/mL to about 24 μg/mL, about 2 μg/mL to about 22 μg/mL, about 2 μg/mL to about 20 μg/mL, about 2 μg/mL to about 19 μg/mL, about 2 μg/mL to about 18 μg/mL, about 2 μg/mL to about 17 μg/mL, about 2 μg/mL to about 16 μg/mL, about 2 μg/mL to about 15 μg/mL, about 2 μg/mL to about 14 μg/mL, about 2 μg/mL to about 13 μg/mL, about 2 μg/mL to about 12 μg/mL, about 2 μg/mL to about 11 μg/mL, about 2 μg/mL to about 10 μg/mL, about 2 μg/mL to about 9.5 μg/mL, about 2 μg/mL to about 9 μg/mL, about 2 μg/mL to about 8.5 μg/mL, about 2 μg/mL to about 8 μg/mL, about 2 μg/mL to about 7.5 μg/mL, about 2 μg/mL to about 7 μg/mL, about 2 μg/mL to about 6.5 μg/mL, about 2 μg/mL to about 6 μg/mL, about 2 μg/mL to about 5.5 μg/mL, about 2 μg/mL to about 5 μg/mL, about 2 μg/mL to about 4.8 μg/mL, about 2 μg/mL to about 4.6 μg/mL, about 2 μg/mL to about 4.4 μg/mL, about 2 μg/mL to about 4.2 μg/mL, about 2 μg/mL to about 4 μg/mL, about 2 μg/mL to about 3.8 μg/mL, about 2 μg/mL to about 3.6 μg/mL, about 2 μg/mL to about 3.4 μg/mL, about 2 μg/mL to about 3.2 μg/mL, about 2 μg/mL to about 3 μg/mL, about 2 μg/mL to about 2.8 μg/mL, about 2 μg/mL to about 2.6 μg/mL, about 2 μg/mL to about 2.4 μg/mL, about 2 μg/mL to about 2.2 μg/mL, about 10 μg/mL to about 50 μg/mL, about 11 μg/mL to about 50 μg/mL, about 12 μg/mL to about 50 μg/mL, about 13 μg/mL to about 50 μg/mL, about 14 μg/mL to about 50 μg/mL, about 15 μg/mL to about 50 μg/mL, about 16 μg/mL to about 50 μg/mL, about 17 μg/mL to about 50 μg/mL, about 18 μg/mL to about 50 μg/mL, about 19 μg/mL to about 50 μg/mL, about 20 μg/mL to about 50 μg/mL, about 22 μg/mL to about 50 μg/mL, about 24 μg/mL to about 50 μg/mL, about 26 μg/mL to about 50 μg/mL, about 28 μg/mL to about 50 μg/mL, about 30 μg/mL to about 50 μg/mL, about 32 μg/mL to about 50 μg/mL, about 34 μg/mL to about 50 μg/mL, about 36 μg/mL to about 50 μg/mL, about 38 μg/mL to about 50 μg/mL, about 40 μg/mL to about 50 μg/mL, about 42 μg/mL to about 50 μg/mL, about 44 μg/mL to about 50 μg/mL, about 46 μg/mL to about 50 μg/mL, about 48 μg/mL to about 50 μg/mL, about 10 μg/mL to about 45 μg/mL, about 10 μg/mL to about 40 μg/mL, about 10 μg/mL to about 38 μg/mL, about 10 μg/mL to about 36 μg/mL, about 10 μg/mL to about 34 μg/mL, about 10 μg/mL to about 32 μg/mL, about 10 μg/mL to about 30 μg/mL, about 10 μg/mL to about 28 μg/mL, about 10 μg/mL to about 26 μg/mL, about 10 μg/mL to about 24 μg/mL, about 10 μg/mL to about 22 μg/mL, about 10 μg/mL to about 20 μg/mL, about 10 μg/mL to about 19 μg/mL, about 10 μg/mL to about 18 μg/mL, about 10 μg/mL to about 17 μg/mL, about 10 μg/mL to about 16 μg/mL, about 10 μg/mL to about 15 μg/mL, about 10 μg/mL to about 14 μg/mL, about 10 μg/mL to about 13 μg/mL, about 10 μg/mL to about 12 μg/mL, about 10 μg/mL to about 11 μg/mL, about 2.2 μg/mL to about 15 μg/mL, about 2.4 μg/mL to about 15 μg/mL, about 2.6 μg/mL to about 15 μg/mL, about 2.8 μg/mL to about 15 μg/mL, about 3 μg/mL to about 15 μg/mL, about 3.2 μg/mL to about 9150 μg/mL, about 3.4 μg/mL to about 15 μg/mL, about 3.6 μg/mL to about 15 μg/mL, about 3.8 μg/mL to about 15 μg/mL, about 4 μg/mL to about 15 μg/mL, about 4.5 μg/mL to about 15 μg/mL, about 5 μg/mL to about 15 μg/mL, about 5.5 μg/mL to about 15 μg/mL, about 6 μg/mL to about 15 μg/mL, about 6.5 μg/mL to about 15 μg/mL, about 7 μg/mL to about 15 μg/mL, about 7.5 μg/mL to about 15 μg/mL, about 8 μg/mL to about 15 μg/mL, about 8.5 μg/mL to about 15 μg/mL, about 9 μg/mL to about 15 μg/mL, about 9.5 μg/mL to about 15 μg/mL, about 10 μg/mL to about 15 μg/mL, about 11 μg/mL to about 15 μg/mL, about 12 μg/mL to about 15 μg/mL, about 13 μg/mL to about 15 μg/mL, or about 14 μg/mL to about 15 μg/mL. The concentration of the lauroyl arginate ethyl ester can be about 1 μg/mL, about 1.2 μg/mL, about 1.4 μg/mL, about 1.6 μg/mL, about 1.8 μg/mL, about 2.0 μg/mL, about 2.2 μg/mL, about 2.4 μg/mL, about 2.6 μg/mL, about 2.8 μg/mL, about 3 μg/mL, about 3.2 μg/mL, about 3.4 μg/mL, about 3.6 μg/mL, about 3.8 μg/mL, about 4 μg/mL, about 4.2 μg/mL, about 4.4 μg/mL, about 4.6 μg/mL, about 4.8 μg/mL, about 5 μg/mL, about 5.5 μg/mL, about 6 μg/mL, about 6.5 μg/mL, about 7 μg/mL, about 7.5 μg/mL, about 8 μg/mL, about 8.5 μg/mL, about 9 μg/mL, about 9.5 μg/mL, about 10 μg/mL, about 15 μg/mL, about 20 μg/mL, about 25 μg/mL, about 30 μg/mL, about 35 μg/mL, about 40 μg/mL, about 45 μg/mL, about 50 μg/mL, about 55 μg/mL, about 60 μg/mL, about 65 μg/mL, about 70 μg/mL, about 75 μg/mL, about 80 μg/mL, about 85 μg/mL, about 90 μg/mL, about 95 μg/mL, about 100 μg/mL, about 110 μg/mL, about 120 μg/mL, about 130 μg/mL, about 140 μg/mL, about 150 μg/mL, about 160 μg/mL, about 170 μg/mL, about 180 μg/mL, about 190 μg/mL, about 200 μg/mL, about 220 μg/mL, about 240 μg/mL, about 260 μg/mL, about 280 μg/mL, about 300 μg/mL, about 330 μg/mL, about 360 μg/mL, about 390 μg/mL, about 400 μg/mL, about 440 μg/mL, about 480 μg/mL, about 500 μg/mL, about 550 μg/mL, about 600 μg/mL, about 650 μg/mL, about 700 μg/mL, about 750 μg/mL, about 800 μg/mL, about 850 μg/mL, about 900 μg/mL, about 950 μg/mL, or about 1 mg/mL. In some embodiments, the concentration of the lauroyl arginate ethyl ester in the wound irrigation solution is between about 1 μg/mL to about 200 μg/mL. In some embodiments, the concentration of the lauroyl arginate ethyl ester in the wound irrigation solution is between about 2 μg/mL to about 100 μg/mL. In some embodiments, the concentration of the lauroyl arginate ethyl ester in the wound irrigation solution is between about 2 μg/mL to about 15 μg/mL. In some embodiments, the concentration of the lauroyl arginate ethyl ester in the wound irrigation solution is between about 10 μg/mL to about 50 μg/mL. In some embodiments, the concentration of the lauroyl arginate ethyl ester in the wound irrigation solution is about 7.5 μg/mL or about 30 μg/mL.

The wound irrigation solution can contain any ratio of two antiseptic agents. The ratio (weight-weight ratio (w/w ratio), ratio of concentrations) of two antiseptic agents can be about 1:1, about 1:1.25, about 1:1.5, about 1:1.75, about 1:2, about 1:2.25, about 1:2.5, about 1:2.75, about 1:3, about 1:3.25, about 1:3.5, about 1:3.75, about 1:4, about 1:4.25, about 1:4.5, about 1:4.75, about 1:5, about 1:5.25, about 1:5.5, about 1:5.75, about 1:6, about 1:6.25, about 1:6.5, about 1:6.75, about 1:7, about 1:7.25, about 1:7.5, about 1:7.75, about 1:8, about 1:8.25, about 1:8.5, about 1:8.75, about 1:9, about 1:9.25, about 1:9.5, about 1:9.75, about 1:10, about 1:11, about 1:12, about 1:13, about 1:14, about 1:15, about 1:16, about 1:17, about 1:18, about 1:19, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, about 1:100, about 2:3, about 3:4, about 3:5, about 4:5, about 5:6, about 6:7, about 7:8, about 7:9, about 8:9, about 7:10, or about 9:10. In some embodiments, the ratio of two antiseptic agents is about 1:66.67. In some embodiments, the ratio of two antiseptic agents is about 1:16.67.

Wound irrigation solutions used in the methods and devices described herein can be synergistically antimicrobial (e.g., microbiocidal or microbiostatic, synergistic with respect to two or more antiseptic agents contained in the solution) to any microorganism (e.g., any microorganism described herein), including but not limited to, a virus, a bacterium, a fungus, a protozoan, or combinations thereof. One way to measure synergy is by fractional inhibitory concentration (FIC) index. FIC index can be calculated by the following Equation 1:

$$FIC = \frac{AA1MIC \text{ in combination with } AA2}{AA1MIC \text{ alone}} + \frac{AA2MIC \text{ in combination with } AA1}{AA2MIC \text{ alone}}, \quad \text{(Equation 1)}$$

wherein AA1 is a first antiseptic agent and AA2 is a second antiseptic agent. Irrigation solutions described herein can be synergistically antimicrobial with an FIC index of at most about 0.5, at most about 0.45, at most about 0.40, at most about 0.35, at most about 0.30, at most about 0.25, at most about 0.20, at most about 0.15, or at most about 0.1. In some embodiments, the FIC index is at most about 0.5.

Wound irrigation solutions can contain a combination of two or more antiseptic agents that are synergistically microbiocidal or microbiostatic to any microorganism (e.g., any fungus, any bacterium, any protozoan, any virus, any microorganism described herein). For example, the wound irrigation solution can be synergistically microbiocidal or microbiostatic for any one of the following: *Acinetobacter* spp., *Bordetella* spp., *Burkholderia* spp., *Campylobacter* spp., *Clostridioides difficile, Cutibacterium* spp. (e.g., *Cutibacterium acnes, Cutibacterium* avidum, *Cutibacterium granulosum, Cutibacterium modestum, Cutibacterium namnetense, Cutibacterium porci*), *Enterobacterales* spp., *Enterococci* spp., *Lactobacillus* spp. (*L. rhamnosus, L. acidophilus, L. casei, L. fermentum, L. paracasei, L. corneformis*), *Mycoplasma* spp., *Neisseria* spp., *Pseudomonas* spp., *Ralstonia* spp., *Staphylococcus* spp., *Streptococcus* spp., or combinations thereof. In some embodiments, the wound irrigation solution is synergistically microbiocidal or microbiostatic to a fungus. In some embodiments, the wound irrigation solution is synergistically microbiocidal or microbiostatic to a bacterium. In some embodiments, the wound irrigation solution is synergistically microbiocidal or microbiostatic to a virus. In some embodiments, the wound irrigation solution is synergistically microbiocidal or microbiostatic to a protozoan. In some embodiments, the wound irrigation solution is synergistically microbiocidal or microbiostatic to a fungus and/or a bacterium. In some embodiments, the wound irrigation solution is synergistically microbiocidal or microbiostatic to a *Candida* species. In some embodiments, the wound irrigation solution is synergistically microbiocidal or microbiostatic to an *E. coli.* In some embodiments, the wound irrigation solution is synergistically microbiocidal or microbiostatic to *Staphylococcus* species. In some embodiments, the wound irrigation solution is synergistically microbiocidal or microbiostatic to *Ralstonia* species. In some embodiments, the wound irrigation solution is synergistically micobiocidal or microbiostatic to *Pseudomonas* species. In some embodiments, the wound irrigation solution is synergistically microbiocidal or microbiostatic to *Candida* species, *E. coli, Staphylococcus*

*species, Ralstonia species, Pseudomonas* species, or a combination thereof. In some embodiments, the wound irrigation solution is synergistically microbiocidal or microbiostatic to *E. coli, P. aeruginosa*, or a combination thereof. In some embodiments, the wound irrigation solution is synergistically microbiocidal or microbiostatic to *C. albicans, E. coli*, methicillin-resistant *Staphylococcus aureus, Staphylococcus aureus, Staphylococcus epidermidis, Ralstonia pickettii, P. aeruginosa*, or a combination thereof. In some embodiments, the wound irrigation solution is synergistically microbiocidal or microbiostatic to *C. albicans*. In some embodiments, the wound irrigation solution is synergistically microbiocidal or microbiostatic to *E. coli*. In some embodiments, the wound irrigation solution is synergistically microbiocidal or microbiostatic to *Staphylococcus aureus*. In some embodiments, the wound irrigation solution is synergistically microbiocidal or microbiostatic to methicillin-resistant *Staphylococcus aureus*. In some embodiments, the wound irrigation solution is synergistically microbiocidal or microbiostatic to *Staphylococcus epidermidis*. In some embodiments, the wound irrigation solution is synergistically microbiocidal or microbiostatic to *Ralstonia pickettii*. In some embodiments, the wound irrigation solution is synergistically microbiocidal or microbiostatic to *P. aeruginosa*. In some embodiments, the wound irrigation solution is synergistically microbiocidal or microbiostatic to a *Cutibacterium* species (e.g., *Cutibacterium acnes*). In some embodiments, the wound irrigation solution is synergistically microbiocidal or microbiostatic to a *Lactobacillus* species (*L. rhamnosus*).

Wound irrigation solutions described herein can comprise any number of different antiseptic agents including, but not limited to, 2, 3, 4, 5, 6, 7, 8, 9, or 10. The number of antiseptic agents can be between 2 and 3, between 2 and 4, between 2 and 5, between 2 and 6, between 2 and 7, between 2 and 8, between 2 and 9, between 2 and 10, between 3 and 4, between 3 and 5, between 3 and 6, between 3 and 7, between 3 and 8, between 3 and 9, or between 3 and 10.

A microbial burden (e.g., a bacterial burden, a fungal burden, a viral burden, a protozoal burden, a microbial burden of a wound) of any microorganism (e.g., the microorganisms disclosed herein) treated with a method or device described herein can be reduced by any degree. One way to measure microbial burden is by colony forming units (CFU). The microbial burden can be reduced by any magnitude (e.g., the CFUs can be reduced by any magnitude) following treatment with a method or device described herein. The magnitude of microbial burden can be reduced by about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 40-fold, about 50-fold, about 60-fold, about 70-fold, about 80-fold, about 90-fold, about 100-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1200-fold, about 1400-fold, about 1600-fold, about 1800-fold, about 2000-fold, about 3000-fold, about 4000-fold, about 5000-fold, about 6000-fold, about 7000-fold, about 8000-fold, about 9000-fold, or about 10000-fold. The magnitude of microbial burden can be reduced by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least at least about 30-fold, at least about 40-fold, at least about 50-fold, at least about 60-fold, at least about 70-fold, at least about 80-fold, at least about 90-fold, at least about 100-fold, at least about 120-fold, at least about 130-fold, at least about 140-fold, at least about 150-fold, at least about 160-fold, at least about 170-fold, at least about 180-fold, at least about 190-fold, at least about 200-fold, at least about 250-fold, at least about 300-fold, at least about 350-fold, at least about 400-fold, at least about 450-fold, at least about 500-fold, at least about 550-fold, at least about 600-fold, at least about 650-fold, at least about 700-fold, at least about 750-fold, at least about 800-fold, at least about 850-fold, at least about 900-fold, at least about 950-fold, at least about 1000-fold, at least about 1200-fold, at least about 1400-fold, at least about 1600-fold, at least about 1800-fold, at least about 2000-fold, at least about 3000-fold, at least about 4000-fold, at least about 5000-fold, at least about 6000-fold, at least about 7000-fold, at least about 8000-fold, at least about 9000-fold, or at least about 10000-fold. Wound irrigation solutions in methods and devices described herein can reduce a microbial burden (e.g., a microbial burden of a wound, a fungal burden, a bacterial burden, a viral burden, or a protozoal burden, the burden of any microorganism described herein) to any amount of microorganism (e.g., any number of colony forming units (CFUs)).

Wound irrigation solutions can decrease the microbial burden (e.g., the burden of any bacterium, fungus, virus, protozoa described herein) to a number of CFUs per gram of tissue that is at most about $10^7$, at most about $5\times10^6$, at most about $10^6$, at most about $5\times10^5$, at most about $10^5$, at most about $5\times10^4$, at most about $10^4$, at most about $5\times10^3$, at most about $10^3$, at most about $5\times10^2$, at most about $10^2$, at most about $5\times10^1$, at most about $10^1$, at most about 5, at most about 1, or zero.

Wound irrigation solutions described herein containing two or more antiseptic agents (e.g., containing a synergistic combination of two or more antiseptic agents) can reduce the amount of irrigation time required to reduce a microbial burden (e.g., a microbial burden of a wound, a fungal burden, a bacterial burden, a viral burden, a protozoal burden, a burden of any microorganism described herein to any amount or magnitude described herein). The reduction in irrigation time can be measured by comparison to an analogous method or device that uses a wound irrigation solution that contains only one antiseptic agent present at an equivalent concentration (e.g., contains only chlorhexidine without an additional antiseptic agent, contains only lauroyl arginate ethyl ester or a pharmaceutically acceptable salt thereof without an additional antiseptic agent, contains a non-synergistic combination of two or more antiseptic agents). The degree of irrigation time reduction can be at least about 15%, at least about 20%, at least about 25%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 99.5%. In some embodiments, an amount of irrigation time required to reduce a bacterial burden of the wound or a fungal burden of the wound by at least about 100-fold compared to an analogous method using an alternative irrigation solution comprising the same concentration of chlorhexidine without an additional antiseptic agent is reduced by at least about 50%.

A wound can be irrigated for any duration of time (e.g., any irrigation time). The amount of irrigation time required to reduce a microbial burden (e.g., a bacterial burden, a fungal burden, a viral burden, a protozoal burden, reduce a microbial burden by any magnitude described herein) can be within 30 minutes, 29 minutes, 28 minutes, 27 minutes, 26 minutes, 25 minutes, 24 minutes, 23 minutes, 22 minutes, 21 minutes, 20 minutes, 19 minutes, 18 minutes, 17 minutes, 16 minutes, 15 minutes, 14 minutes, 13 minutes, 12 minutes, 11 minutes, 10 minutes, 9 minutes, 8 minutes, 7 minutes, 6 minutes, 5 minutes, 4 minutes, 3.5 minutes, 3 minutes, 2.5 minutes, 2 minutes, 1.5 minutes, 1 minute, 45 seconds, 30 seconds, or 15 seconds. The required irrigation time can be between about 1 minute to about 30 minutes, about 1 minute to about 25 minutes, about 1 minute to about 20 minutes, about 1 minute to about 15 minutes, about 1 minute to about 10 minutes, about 1 minute to about 5 minutes, or about 1 minute to about 3 minutes. In some embodiments, the amount of irrigation time required is within 15 minutes. In some embodiments, wherein an amount of irrigation time required to reduce a bacterial burden of the wound or a fungal burden of the wound by at least 100-fold compared to an analogous method using an alternative irrigation solution comprising the same concentration of chlorhexidine without an additional antiseptic agent is reduced by at least about 50% and is within 15 minutes, within 10 minutes, within 5 minutes, within 3 minutes, or within 1 minute.

As described above, in some embodiments, the device described herein is used to deliver an active agent (e.g., a synergistic combination of two antiseptic agents), such as an antimicrobial agent, to a target site, such as a wound. Subsequent to the administration of the active agent, the site can then be flushed with, for example, saline to remove at least any excess of the active agent. Flushing of the site can occur within any period of time following the administration of the wound irrigation solution. The flushing of the site can occur within a period of time that is about 30 seconds, about 45 seconds, about 1 minute, about 1.5 minutes, about 2 minutes, about 2.5 minutes, about 3 minutes, about 3.5 minutes, about 4 minutes, about 4.5 minutes, about 5 minutes, about 5.5 minutes, about 6 minutes, about 6.5 minutes, about 7 minutes, about 7.5 minutes, about 8 minutes, about 8.5 minutes, about 9 minutes, about 9.5 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 24 minutes, about 26 minutes, about 28 minutes, or about 30 minutes. In some embodiments flushing occurs within five minutes of the administration of the wound irrigation solution. Flushing of the site can occur following the administration of the wound irrigation solution in a time period between about 30 seconds and about 45 seconds, about 30 seconds and about 1 minute, about 30 seconds and about 1.5 minutes, about 30 seconds and about 2 minutes, about 30 seconds and about 2.5 minutes, about 30 seconds and about 3 minutes, about 30 seconds and about 3.5 minutes, about 30 seconds and about 4 minutes, about 30 seconds and about 4.5 minutes, about 30 seconds and about 5 minutes, about 30 seconds and about 5.5 minutes, about 30 seconds and about 6 minutes, about 30 seconds and about 6.5 minutes, about 30 seconds and about 7 minutes, about 30 seconds and about 7.5 minutes, about 30 seconds and about 8 minutes, about 30 seconds and about 8.5 minutes, about 30 seconds and about 9 minutes, about 30 seconds and about 9.5 minutes, about 30 seconds and about 10 minutes, about 30 seconds and about 15 minutes, about 30 seconds and about 20 minutes, about 1 minute to about 30 minutes, about 2 minutes to about 30 minutes, about 3 minutes to about 30 minutes, about 4 minutes to about 30 minutes, about 5 minutes to about 30 minutes, about 6 minutes to about 30 minutes, about 7 minutes to about 30 minutes, about 8 minutes to about 30 minutes, about 9 minutes to about 30 minutes, about 10 minutes to about 30 minutes, about 15 minutes to about 30 minutes, about 20 minutes to about 30 minutes, about 25 minutes to about 30 minutes, about 5 minutes to about 30 minutes, about 1 minute to about 2 minutes, about 1 minute to about 3 minutes, about 1 minute to about 4 minutes, about 1 minute to about 5 minutes, about 1 minute to about 6 minutes, about 1 minute to about 7 minutes, about 1 minute to about 8 minutes, about 1 minute to about 9 minutes, about 1 minute to about 10 minutes, about 1 minute to about 15 minutes, about 1 minute to about 20 minutes, about 1 minute to about 25 minutes, about 1 minute to about 30 minutes, about 3 minutes to about 4 minutes, about 3 minutes to about 5 minutes, about 3 minutes to about 6 minutes, about 3 minutes to about 7 minutes, about 3 minutes to about 8 minutes, about 3 minutes to about 9 minutes, about 3 minutes to about 10 minutes, about 3 minutes to about 15 minutes, about 3 minutes to about 20 minutes, about 3 minutes to about 25 minutes, or about 3 minutes to about 30 minutes. In some embodiments, flushing occurs within one to three minutes of the administration of the wound irrigation solution. In this way, any potential toxicity, sensitivity, contact dermatitis and/or allergy associated with the active agent (e.g., an antiseptic agent) can be reduced or eliminated. In the case of a chlorhexidine or lauroyl arginate ethyl ester, rinsing with an irrigation fluid removes excess chlorhexidine or lauroyl arginate ethyl ester that has not bound to, for example, proteins of the skin or other tissue.

In yet another embodiment, a diagnostic agent can be administered using the devices and methods described herein. The diagnostic agent may be, for example, an antibody, protein, or polynucleotide that binds to a target biomolecule. Any such binding may then be visualized utilizing technologies known to those skilled in the art. These technologies include, for example, the use of fluorophores or other labels that can be visualized either by the naked eye or through appropriate detection instruments. The diagnostic applications of the devices and methods described herein include the detection of bacteria, viruses, parasites, and other pathogens. Cancer cells can also be visualized using the diagnostic methods described herein.

In yet another embodiment, the device and method can be used to deliver growth factors and/or protease inhibitors to a target site. Such growth factors and/or protease inhibitors, which can, for example, expedite the healing of wounds, are well known to those skilled in the art.

In yet another embodiment, the methods described herein can be used to deliver oxygenated water and/or "enhanced water" to a target site. The enhanced water can be that which is described in, for example, published U.S. Patent Application Publication US20050191364A1 and the references cited therein (all of which are incorporated herein by reference in their entireties). The use of methods described herein for the effective delivery of such oxygenated or enhanced water can be used to promote tissue healing and reduce infections.

In a further embodiment, the devices, and methods described herein can be used to efficiently deliver antimicrobial peptides (AMPs) to a target site. AMPs are well known in the art. Antimicrobial peptides are predominantly small polypeptides that inhibit the growth of microbes. As effectors of innate immunity, antimicrobial peptides directly kill a broad spectrum of bacteria, fungi, and viruses. In addition, these peptides modify the local inflammatory response and activate mechanisms of cellular and adaptive immunity. Cathelicidins and defensins comprise the major families of AMPs in the skin, although other cutaneous peptides, such as proteinase inhibitors, chemokines, and neuropeptides, also demonstrate antimicrobial activity. See, for example, Braff, M. et al., (2005) "Cutaneous Defense Mechanisms by Antimicrobial Peptides," *J Invest Dermatol,* 125:9-13.

The Drug Delivery Device

In some embodiments, the device described herein provides a reservoir housing containing a solution with two or more active agents (e.g., a wound irrigation solution), wherein the reservoir housing has attached to it a discharge means having a plurality of ports through which a sufficient volume of the wound irrigation solution can pass at an appropriate pressure for effective delivery of the wound irrigation solution, including the active agent, to a target site.

FIG. 1 shows an exemplary device, wherein the device contains a squeezable reservoir housing having a wall 60 that forms a reservoir that can contain therein an irrigation material including a medicinal agent (e.g., an antiseptic agent, a chlorhexidine, lauroyl arginate ethyl ester or a pharmaceutically acceptable salt thereof, a synergistic combination of antiseptic agents). The reservoir housing has a mouth 62, which communicates the reservoir to the outside of the housing. Disposed over the reservoir housing mouth, and affixed to the reservoir housing mouth is a discharge means 80, 100.

In some embodiments, the nozzle(s) of devices described herein are specifically designed to reduce the pressure loss as the fluid (e.g., the wound irrigation solution) leaves the reservoir housing.

In some embodiments, each nozzle acts as a jet through which fluid is forced, under pressure, to achieve velocities and pressures appropriate for efficient irrigation. The nozzles are designed to reduce friction and turbulence and facilitate achieving sufficient irrigation pressures with minimal operator effort.

In certain embodiments of the devices describe herein, the nozzle is a "shaped" nozzle defined by a shaped passageway (see FIGS. 2A-2D and 3). As used herein, the "shaped passageway" extends the length of the nozzle and is defined by a cylindrical bore 98 that narrows as it approaches the outlet port 96. The shaped passageway of the nozzle limits the generation of turbulence in the wound irrigation fluid as it passes through the nozzle(s) during the operation of the wound irrigation devices described herein. Therefore, fluid passing through the nozzle experiences laminar flow (or at least a reduction in turbulence) as it passes through and exits the nozzle. Thus, as used herein, reference to the "shaped passageway" refers to a nozzle with a passageway where the cross-sectional area of the inlet port 102 is greater than the cross-sectional area at or near the outlet port 96 wherein the inlet port is curved (not squared off), and the turbulence through the nozzle is less than the turbulence of a nozzle of the same or similar size but having a "squared-off" inlet port and/or constant diameter passageway. This shaped nozzle has been found to be particularly advantageous for achieving desired irrigation fluid pressures and velocities according to the methods and devices described herein. The description of nozzles set forth in WO 2005/030297 is incorporated herein in its entirety by reference.

The nozzle passage area 98 is preferably defined by a funnel shape having a portion with a curved surface, where the nozzle cross-section decreases from an upstream wider end 102 to the downstream end 96.

Figure 2C:
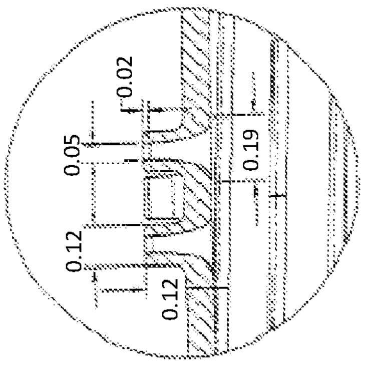
FIGS. 2A-2D show embodiments of the ports of a device described herein.
Figure 2D:
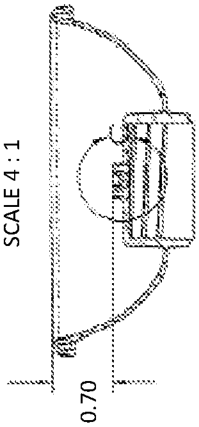
Figure 2A:
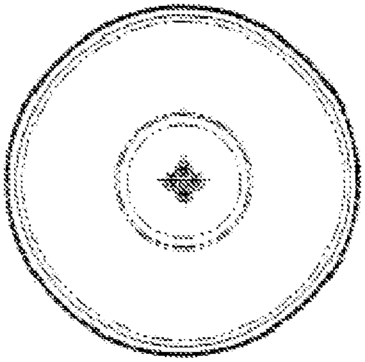
Figure 2B:
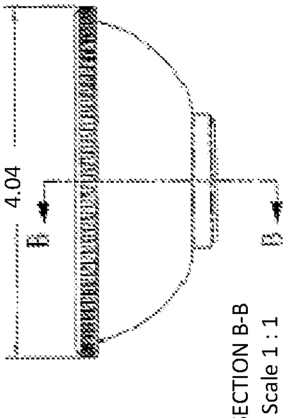
Figure 3:
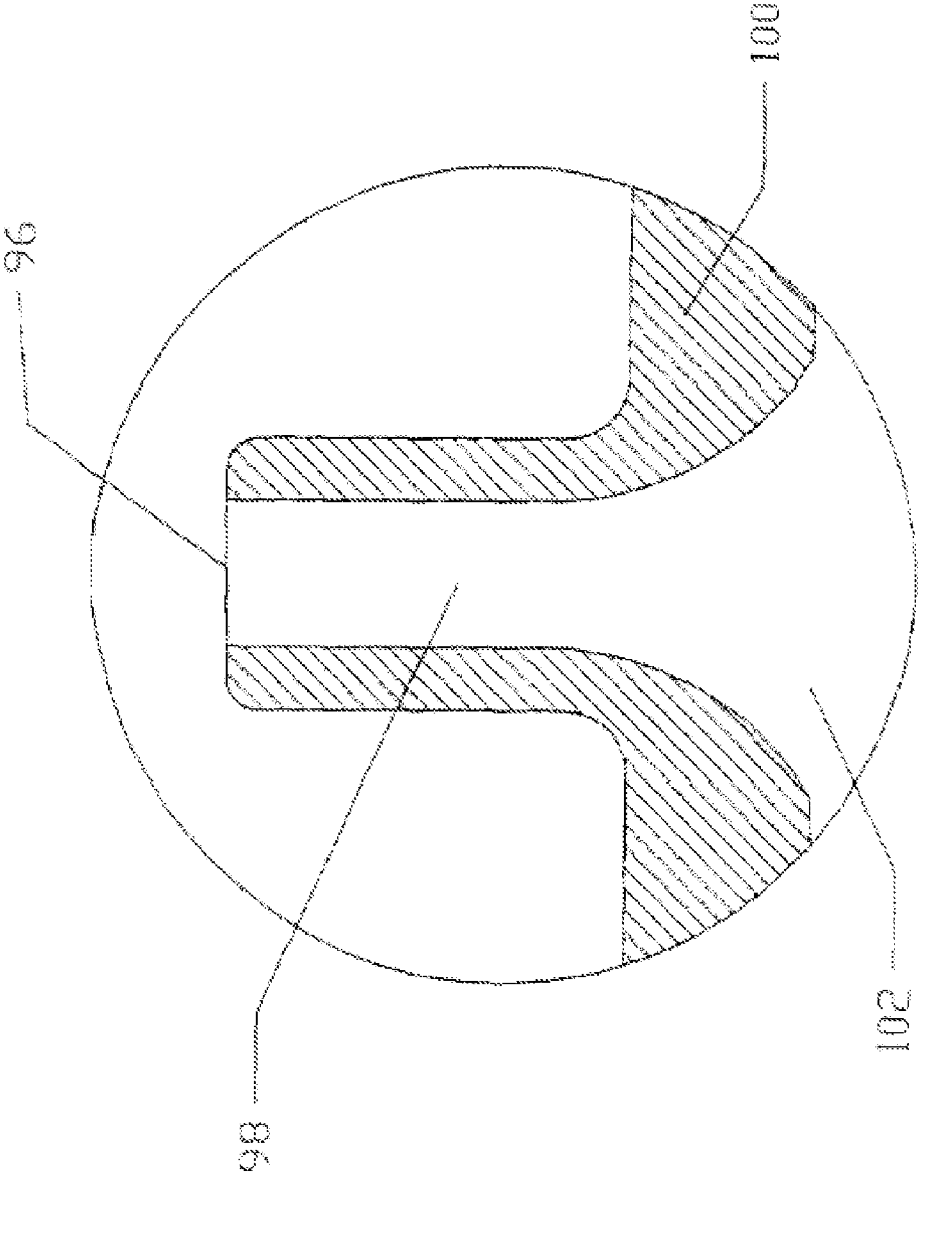
FIG. 3 shows a cross-sectional view of a port of a device described herein.

FIGS. 2A-2D show a specific embodiment of the elongated, shaped nozzles of a device described herein. In FIG. 2B the conical shaped nozzle is 0.2 inches long (from inlet port to outlet port).

As would be appreciated by a person skilled in the art having the benefit of the current disclosure, the nozzles of the devices described herein can be formed within the material of the discharge means. Thus, if the discharge means is formed of plastic that is sufficiently thick, then the nozzles may simply pass through the material of the discharge means. Alternatively, the nozzles may extend from either side of the discharge means.

In certain embodiments, the discharge means is detachably affixed to the reservoir housing mouth. In such embodiments, the reservoir mouth can include connecting means such as threads, snap fits, grooves, or other mechanical connection configurations for operably connecting the reservoir housing mouth to the discharge means.

The wall of the reservoir housing can be made or molded from any material that is preferably rigid enough to stand upright when the reservoir is filled with wound irrigation solution. In a typical embodiment, the reservoir housing is formed by a molded plastic, which is pliable enough so that the wall of the reservoir housing can be squeezed or compressed by hand to exert pressure on the contents of the reservoir. In some embodiments, the reservoir housing comprises a plastic material that is pliable enough to squeeze by hand and which also has sufficient resilience to return to its original shape when no longer compressed or squeezed. In some embodiments, the reservoir housing returns to the original shape very quickly when no longer compressed or squeezed.

The horizontal cross-sectional shape of the reservoir housing can be circular, square, rectangular, or other geometric shapes as desired or as already available. The walls can be tapering toward one end or the other. Alternatively, other shapes can be made for the reservoir housing according to and adapted for a particular use. For example, part of the reservoir housing wall can be slightly rounded as in a general hourglass shape and/or can be molded for ergonomics to easily fit a hand or otherwise to facilitate handling or compressing the reservoir housing. The reservoir formed by the housing can hold any volume of irrigation solution. The volume of irrigation solution can be between about 50 mL to about 2000 mL, about 100 mL to about 2000 mL, about 150 mL to about 2000 mL, about 200 mL to about 2000 mL, about 250 mL to about 2000 mL, about 300 mL to about 2000 mL, about 350 mL to about 2000 mL, about 400 mL to about 2000 mL, about 450 mL to about 2000 mL, about 500 mL to about 2000 mL, about 550 mL to about 2000 mL, about 600 mL to about 2000 mL, about 650 mL to about 2000 mL, about 700 mL to about 2000 mL, about 750 mL to about 2000 mL, about 800 mL to about 2000 mL, about 850 mL to about 2000 mL, about 900 mL to about 2000 mL, about 950 mL to about 2000 mL, about 1000 mL to about 2000 mL, about 1100 mL to about 2000 mL, about 1200 mL to about 2000 mL, about 1300 mL to about 2000 mL, about 1400 mL to about 2000 mL, about 1500 mL to about 2000 mL, about 1600 mL to about 2000 mL, about 1700 mL to about 2000 mL, about 1800 mL to about 2000 mL, about 1900 mL to about 2000 mL, about 100 mL to about 1000 mL, about 200 mL to about 1800 mL, about 300 mL to about 1600 mL, about 400 mL to about 1400 mL, or about 500 mL to about 1000 mL. The reservoir formed by the housing of devices described herein can typically hold a volume of about 100 ml to 1000 ml, preferably about 250 ml to about 750 ml, and most preferably about 500 ml. Any volume of wound irrigation solution can be applied to the wound in the methods described herein. The volume of applied wound irrigation solution can be between about 50 mL to about 2000 mL, about 100 mL to about 2000 mL, about 150 mL to about 2000 mL, about 200 mL to about 2000 mL, about 250 mL to about 2000 mL, about 300 mL to about 2000 mL, about 350 mL to about 2000 mL, about 400 mL to about 2000 mL, about 450 mL to about 2000 mL, about 500 mL to about 2000 mL, about 550 mL to about 2000 mL, about 600 mL to about 2000 mL, about 650 mL to about 2000 mL, about 700 mL to about 2000 mL, about 750 mL to about 2000 mL, about 800 mL to about 2000 mL, about 850 mL to about 2000 mL, about 900 mL to about 2000 mL, about 950 mL to about 2000 mL, about 1000 mL to about 2000 mL, about 1100 mL to about 2000 mL, about 1200 mL to about 2000 mL, about 1300 mL to about 2000 mL, about 1400 mL to about 2000 mL, about 1500 mL to about 2000 mL, about 1600 mL to about 2000 mL, about 1700 mL to about 2000 mL, about 1800 mL to about 2000 mL, about 1900 mL to about 2000 mL, about 100 mL to about 1000 mL, about 200 mL to about 1800 mL, about 300 mL to about 1600 mL, about 400 mL to about 1400 mL, or about 500 mL to about 1000 mL. In some embodiments, about 250 to about 750 mL of wound irrigation solution is applied to the wound. Advantageously, with manual compression, the devices and methods described herein can deliver 500 ml of irrigation fluid in less than 30 seconds and, typically, in 15 to 25 seconds. The fluid is delivered at about 4 to 20 psi. Lower pressures can be used for irrigating eye wounds. For irrigation of wounds in or around the eye, a pressure of about 1 psi to about 5 psi is preferred.

Further, in some embodiments, the reservoir housing comprises at one end a neck portion formed at the mouth of the reservoir housing. The neck portion of the reservoir housing is generally at least slightly smaller in cross sectional area than the reservoir housing. The reservoir housing neck is preferably integrally molded with the reservoir housing but can be formed or molded separately and affixed to the mouth of the reservoir housing. The material used for the neck portion of the reservoir housing can be the same as the material used to make the reservoir housing cylinder. Alternatively, the neck portion can be a different material, for example, a more rigid or sturdy material than the compressible material forming the reservoir housing wall. For example, the material used to make the neck portion can be a metal or a hard plastic, or the like.

With reservoir housing embodiments that include a neck portion, the discharge means is typically disposed over and affixed to the neck portion. In a related embodiment, the neck portion of the reservoir housing can include a connecting means for detachably affixing a discharge means thereto. The connecting means can include threads, latches, grooves, or other mechanical connection configurations for operably connecting the neck portion to the discharge means. The connecting means can be on the outer face of the neck portion, forming a male connecting end, or can be on the inner face forming a female connecting end of the neck portion.

In some embodiments, the discharge means has a plurality of nozzles 70 whereby the wound irrigation solution in the reservoir passes through in a pressurized and directional manner. A backsplash shield 90 can also be provided either with the reservoir housing or with the discharge means.

The back-splash protective shield protects the health care professional (or other user) from back-splash of human and or animal body fluids that are mixed with and splashed from the wound when the wound is contacted by the discharged wound irrigation solution.

As used herein, reference to a "dispersed" stream of solution (e.g., wound irrigation solution) means that the area from which the stream emanates, or the area which it contacts, is larger than that which can be achieved using a typical syringe for irrigation. A typical syringe, as is well known in the art can be, for example, a 16- or 18-gauge syringe. In one embodiment, the dispersed stream can be achieved using multiple nozzles. The nozzles can be presented in a variety of patterns on a discharge means, such as a circular or square pattern or sizes.

In certain embodiments, the discharge means is designed with connecting means that are threads or grooves, which allow for complementary attachment to currently available irrigation solution bottles. Thus, the discharge means of the devices described herein can be interchangeable, when desired, with the screw-cap that is provided with an irrigation solution bottle as are available. The screw-top design of the discharge means provides the operator with the option of using the reservoir housing with the nozzles of the devices described herein or to threadably remove the discharge means and pour out or change the irrigation solution.

Each of the nozzles of the discharge means can be of any desirable size, preferably less than one-eighth inch in diameter and having a size between about a 10-gauge hypodermic needle and about a 30-gauge needle, and most preferably having a size ranging from that of a 16-gauge needle to a 25-gauge needle. Specific dimensions and shapes are shown in FIGS. 2A-2D. The outlet port 96 may have, for example, an inner diameter of about 0.02 to about 0.07 inches. For the venturi shaped nozzle (FIG. 3), the diameter of the inlet port 102 (proximal to the reservoir) can be, for example, from about 0.05 to about 0.30 inches, or more.

Each of the nozzles can be the same size or the nozzles can be different sizes and shapes. The different sizes of nozzles allow for the liquid (e.g., the wound irrigation solution) to be expelled from the discharge means at different pressures. For example, the 16-gauge nozzle allows for a stream having about 6 psi pressure when the device is squeezed by the normal adult; the 25-gauge nozzle provides a pressure of up to about 20 psi from each nozzle.

The shaped nozzles of the devices described herein have the added advantage when compared to other nozzles in that little or no release of irrigation material is permitted without pressure being applied to the irrigation material. For example, if a reservoir housing with shaped nozzles is tipped onto its side or even held upside-down with gravitational pull on the irrigation material through the discharge means, there will be little or no release of irrigation material through the shaped nozzles.

In some embodiments, the discharge means 70 comprises four nozzles. Additionally, to discharge the wound irrigation solution at appropriate pressure, the diameter of the nozzles can be about 0.02 to 0.07 inches in diameter.

From the description of the device herein above, a method of using the device would readily be understood and adaptable by those persons having ordinary skill in the art. The reservoir housing and contents can be stored in a sterile environment, e.g., sterile packaging which is opened immediately prior to use. The reservoir housing can be directed towards the wound and squeezed or compressed to expel or discharge the wound irrigation solution in the desired direction, and at the desired pressure to effect irrigation of a wound to remove contaminants or debris and to deliver the active agent(s). See also the Example 1, provided below.

It would also be understood that the described discharge means can be packaged separately from the reservoir housing. The discharge means is packaged in a sterile environment. In one embodiment, the drug delivery device is provided in a sterile laceration tray. The laceration tray has, in addition to the drug delivery device described herein, other items conveniently provided for treating wounds. Contemplated items that can be included in a laceration tray include, but are not limited to, needle holders (e.g., 5" floor-grade smooth); scissors (e.g., 4.5" floor-grade straight Iris scissors); hemostats (e.g., 5" floor-grade curved mosquito hemostat); forceps (e.g., floor-grade tissue forceps with 1×2 teeth); cups (e.g., 2 oz. medicine cups); syringes (e.g., 10 cc Luer Lock syringe); needles (e.g., 25 gauge×⅝" needle; 27 gauge×1.5" needle; 18 gauge×1.5" needle); dressings (e.g., gauze dressings); drapes (e.g., polylined fenestrated drapes); and towels (e.g., absorbent towels).

In a method of use, where a reservoir housing 60 having discharge means 70 affixed thereto is provided. The discharge means 70 is directed towards the wound, and the reservoir housing 60 is compressed, discharging the wound irrigation solution through the discharge means 70. The wound irrigation solution can be discharged at a range of pressures of about 4-20 lbs/in$^2$, with a preferred pressure of about 7 psi.

The reservoir housing 60 can be compressed manually or via other mechanical means. For example, the operator may compress the reservoir housing either one hand or two hands, to provide increased pressure (e.g., 16 psi). Alternatively, a pressure means can be activated to generate a dispersed stream of wound irrigation solution through the discharge means.

In another method of use, where a reservoir housing 60 and discharge means 70 are provided separately, the discharge means is affixed to the mouth or neck portion of the reservoir housing via complementary connecting means. After the discharge means is affixed to the reservoir housing, the discharge means is directed towards the target site, and the reservoir housing is compressed to discharge a dispersed stream of wound irrigation solution through the nozzles of the discharge means.

Significantly, it is known that more force is required to rid the wound of particles with a small surface area (e.g., bacteria) than to remove particles with a large surface area (e.g., dirt, sand, or vegetation). Minimum recommended volumes of wound irrigation solution vary, but for a moderately sized potentially contaminated wound, for example a laceration 3-6 cm long and less than 2 cm deep, at least 200 to 500 ml, or more should be used. Greater volumes, on the order of one to two liters, may be required for larger or heavily contaminated wounds. Irrigation should continue at least until all visible, loose particulate matter has been removed.

Following are examples that illustrate procedures for practicing the methods described herein. These examples should not be construed as limiting.

Example 1

Methods of Irrigation

When a patient presents a wound to a medical or other health care professional skilled in the art, that medical professional assesses the extent of the injury sustained by the patient, including all other life-threatening injuries. Appropriate action regarding these life-threatening injuries is performed and a history is recorded. All wounds are covered to minimize further contamination until the actual repair process begins.

For examination of the wound, it is assumed that a medical professional would have performed a detailed evaluation of the extent of tissue injury, including but not limited to anatomical area considerations, depth of the wound, type of injury, e.g., crash injury, puncture wound, bites, missiles, cuts with sharp objects, or the like. Included in this examination would be a determination of the type(s) of contamination, time elapsed between the occurrence of the injury to presentation, gross contamination of a wound, and other medical factors associated with an increase incidence of infection (for example, diabetics, AIDS patients, and chemotherapeutic patients).

The wound and surrounding tissue, at the option of the health care professional, could be anesthetized using topical, local, or general anesthetics before the wound-cleansing method begins. Alternatively, an anesthetic may be delivered using the devices and methods described herein.

In one embodiment, a device described herein has a discharge means affixed to a reservoir housing. In some embodiments, the devices described herein can be held in either hand as preferred by the user. Normally, it would be held in the dominant hand in a bottle-holding fashion. This allows the medical care professional to gently open the wound if needed, with the opposite hand, preferably protected by a sterile glove, to expose the depths of the wound.

Once the depths of the wound have been exposed, the end of the reservoir housing having the discharge means affixed thereto is directed towards the wound. Manual or mechanically produced pressure is applied to the reservoir housing to expel the wound irrigation solution with active agent through the nozzles of the discharge means. The wound should be irrigated in this fashion until all visible evidence of contamination has been removed. A potentially contaminated wound of any size should be irrigated with a minimum of 150-300 ml of wound irrigation solution. Heavily contaminated or larger wounds may require 2-3 liters of wound irrigation solution. The health care professional could vary the angle of the discharged wound irrigation solution from the discharge means in reference to the wound to further assist with the dislodgement of contaminants.

Following an initial irrigation of the wound, a reexamination of the wound should be undertaken. The wound should be explored to its base to ascertain that no visible foreign bodies or contaminants remain. If foreign bodies or contaminants are found, the irrigation process should be repeated followed by a re-examination. This may continue for several cycles.

Once irrigation has been completed, e.g., no visible contaminants remain, the damaged tissue would be repaired in a standard accepted fashion.

Any skin wounds such as cuts, scrapes, surgical wounds, punctures, and abrasions and the like are suitable for irrigation according to the devices and methods described herein.

Example 2

Routes of Administration

Table 1 provides a listing of various routes of administration that can be used according to the methods and devices described herein.

TABLE 1

| Routes of Administration | |
|---|---|
| Delivery Route | Description |
| AURICULAR (OTIC) | Administration to or by way of the ear. |
| BUCCAL | Administration directed toward the cheek, generally from within the mouth. |
| CONJUNCTIVAL | Administration to the conjunctiva, the delicate membrane that lines the eyelids and covers the exposed surface of the eyeball. |
| CUTANEOUS | Administration to the skin. |
| DENTAL | Administration to a tooth or teeth. |
| ENDOCERVICAL | Administration within the canal of the cervix uteri. |
| ENDOSINUSIAL | Administration within the nasal sinuses of the head. |
| ENDOTRACHEAL | Administration directly into the trachea. |
| ENTERAL | Administration directly into the intestines. |
| EPIDURAL | Administration upon or over the dura mater. |
| EXTRA-AMNIOTIC | Administration to the outside of the membrane enveloping the fetus |
| EXTRACORPOREAL | Administration outside of the body. |
| INFILTRATION | Administration that results in substances passing into tissue spaces or into cells. |
| INTERSTITIAL | Administration to or in the interstices of a tissue. |
| INTRA-ABDOMINAL | Administration within the abdomen. |
| INTRA-ARTICULAR | Administration within a joint. |
| INTRABILIARY | Administration within the bile, bile ducts or gallbladder. |
| INTRABRONCHIAL | Administration within a bronchus. |
| INTRACARDIAC | Administration with the heart. |
| INTRACARTILAGINOUS | Administration within a cartilage; endochondral. |
| INTRACAVERNOUS | Administration within a pathologic cavity, such as occurs in the lung in tuberculosis. |
| INTRACAVITARY | Administration within a non-pathologic cavity, such as that of the cervix, uterus, or penis, or such as that which is formed as a result of a wound. |
| INTRACEREBRAL | Administration within the cerebrum. |
| INTRACORPORUS CAVERNOSUM | Administration within the dilatable spaces of the corpus cavernosa of the penis. |
| INTRADUCTAL | Administration within the duct of a gland. |
| INTRADUODENAL | Administration within the duodenum. |
| INTRADURAL | Administration within or beneath the dura. |
| INTRAESOPHAGEAL | Administration within the esophagus. |
| INTRAGASTRIC | Administration within the stomach. |
| INTRAILEAL | Administration within the distal portion of the small intestine, from the jejunum to the cecum. |
| INTRALESIONAL | Administration within or introduced directly into a localized lesion. |
| INTRALUMINAL | Administration within the lumen of a tube. |
| INTRALYMPHATIC | Administration within the lymph. |
| INTRAMEDULLARY | Administration within the marrow cavity of a bone. |
| INTRAMENINGEAL | Administration within the meninges (the three membranes that envelope the brain and spinal cord). |
| INTRAOCULAR | Administration within the eye. |
| INTRAOVARIAN | Administration within the ovary. |
| INTRAPERICARDIAL | Administration within the pericardium. |
| INTRAPERITONEAL | Administration within the peritoneal cavity. |
| INTRAPLEURAL | Administration within the pleura. |
| INTRAPROSTATIC | Administration within the prostate gland. |
| INTRAPULMONARY | Administration within the lungs or its bronchi. |
| INTRASINAL | Administration within the nasal or periorbital sinuses. |
| INTRASPINAL | Administration within the vertebral column. |
| INTRASYNOVIAL | Administration within the synovial cavity of a joint. |
| INTRATENDINOUS | Administration within a tendon. |
| INTRATESTICULAR | Administration within the testicle. |
| INTRATHECAL | Administration within the cerebrospinal fluid at any level of the cerebrospinal axis, including injection into the cerebral ventricles. |
| INTRATHORACIC | Administration within the thorax (internal to the ribs); synonymous with the term endothoracic. |
| INTRATUBULAR | Administration within the tubules of an organ. |
| INTRATUMOR | Administration within a tumor. |
| INTRATYMPANIC | Administration within the auris media. |
| INTRAUTERINE | Administration within the uterus. |
| INTRAVESICAL | Administration within the bladder. |
| INTRAVITREAL | Administration within the vitreous body of the eye. |
| IRRIGATION | Administration to bathe or flush open wounds or body cavities. |
| LARYNGEAL | Administration directly upon the larynx. |
| NASAL | Administration to the nose; administered by way of the nose. |

TABLE 1-continued

| Routes of Administration | |
|---|---|
| Delivery Route | Description |
| NASOGASTRIC | Administration through the nose and into the stomach, usually by means of a tube. |
| OCCLUSIVE DRESSING TECHNIQUE | Administration by the topical route which is then covered by a dressing which occludes the area. |
| OPHTHALMIC | Administration to the external eye. |
| ORAL | Administration to or by way of the mouth. |
| OROPHARYNGEAL | Administration directly to the mouth and pharynx. |
| PERCUTANEOUS | Administration through the skin. |
| PERIARTICULAR | Administration around a joint. |
| PERIDURAL | Administration to the outside of the dura mater of the spinal cord. |
| PERINEURAL | Administration surrounding a nerve or nerves. |
| PERIODONTAL | Administration around a tooth. |
| RECTAL | Administration to the rectum. |
| RESPIRATORY (INHALATION) | Administration within the respiratory tract by inhaling orally or nasally for local or systemic effect. |
| RETROBULBAR | Administration behind the pons or behind the eyeball. |
| SOFT TISSUE | Administration into any soft tissue. |
| SUBARACHNOID | Administration beneath the arachnoid. |
| SUBCONJUNCTIVAL | Administration beneath the conjunctiva. |
| SUBCUTANEOUS | Administration beneath the skin; hypodermic. Synonymous with the term SUBDERMAL. |
| SUBLINGUAL | Administration beneath the tongue. |
| SUBMUCOSAL | Administration beneath the mucous membrane. |
| TOPICAL | Administration to a particular spot on the outer surface of the body. The E2B term TRANSMAMMARY is a subset of the term. |
| TRANSMUCOSAL | Administration across the mucosa. |
| TRANSPLACENTAL | Administration through or across the placenta. |
| TRANSTRACHEAL | Administration through the wall of the trachea. |
| TRANSTYMPANIC | Administration across or through the tympanic cavity. |
| URETERAL | Administration into the ureter. |
| URETHRAL | Administration into the urethra. |
| VAGINAL | Administration into the vagina. |

Example 3

Minimum Inhibitory Concentration Determination for Antiseptics

The minimal inhibitory concentration (MIC, the minimum inhibitory concentration required for 90% growth reduction) of ethyl lauroyl arginate hydrochloride was determined against *S. aureus* (ATCC 6538), *P. aeruginosa* (ATCC 15442), and *E. coli* (ATCC BAA 1427) by serial 2-fold dilution experiments. A solution of chlorhexidine (0.025% w/w) was used as a positive control and comparator. Experiments were performed in triplicate and the average result is shown in Table 2. The MIC of ethyl lauroyl arginate hydrochloride (LAE) that inhibited greater than 90% growth of *S. aureus, P. aeruginosa*, and *E. coli* was 3.75 μg/ml, 30 μg/ml, and g/ml, respectively. The control chlorhexidine (0.025% w/w) showed an average inhibition of 121%, 81%, and 63% for *S. aureus, P. aeruginosa*, and *E. coli*, respectively. Overall, the MIC of ethyl lauroyl arginate hydrochloride (LAE) across all organisms tested (i.e., *S. aureus, P. aeruginosa*, and *E. coli*) ranged between 3.75 μg/ml to 30 μg/mL. This result indicates a great variability in susceptibility to inhibition (e.g., MIC value variability) by ethyl lauroyl arginate hydrochloride (LAE) between different bacterial species.

TABLE 2

| Average Growth Inhibition Testing for Antiseptic Agents | | | | |
|---|---|---|---|---|
| Antiseptic Agent | Microorganism | Concentration (μg/mL) | Average Growth Inhibition (%) | Standard Deviation |
| ethyl lauroyl arginate hydrochloride (LAE) | *S. aureus* (ATCC 6538) | 60 | 93 | 0.0033 |
| | | 30 | 97 | 0.0684 |
| | | 15 | 101 | 0.0015 |
| | | 7.5 | 101 | 0.0016 |
| | | 3.75 | 100 | 0.0163 |
| | | 1.875 | -17 | 0.0499 |
| | | 0.9375 | -1 | 0.0366 |
| | | 0.46875 | 7 | 0.0245 |
| Chlorhexidine gluconate | | 250 | 121 | 0.101 |

TABLE 2-continued

Average Growth Inhibition Testing for Antiseptic Agents

| Antiseptic Agent | Microorganism | Concentration (μg/mL) | Average Growth Inhibition (%) | Standard Deviation |
|---|---|---|---|---|
| ethyl lauroyl arginate hydrochloride (LAE) | *P. aeruginosa* (ATCC 15442) | 60 | 99 | 0.0031 |
| | | 30 | 100 | 0.0004 |
| | | 15 | 2 | 0.0332 |
| | | 7.5 | 5 | 0.0032 |
| | | 3.75 | 4 | 0.0105 |
| | | 1.875 | 2 | 0.0062 |
| | | 0.9375 | 2 | 0.0041 |
| | | 0.46875 | 2 | 0.0112 |
| Chlorhexidine gluconate | | 250 | 81 | 0.0301 |
| ethyl lauroyl arginate hydrochloride (LAE) | *E. coli* (ATCC BAA 1427) | 60 | 99 | 0.0002 |
| | | 30 | 100 | 0.0005 |
| | | 15 | 100 | 0.0005 |
| | | 7.5 | 4 | 0.0076 |
| | | 3.75 | 4 | 0.0107 |
| | | 1.875 | 5 | 0.0025 |
| | | 0.9375 | 6 | 0.002 |
| | | 0.46875 | 3 | 0.0028 |
| Chlorhexidine gluconate | | 250 | 63 | 0.116 |

Example 4

Minimal Bactericidal Concentration Determination for Antiseptics

The minimal bactericidal concentration (MBC) of ethyl lauroyl arginate hydrochloride (LAE) was determined against *S. aureus* (ATCC 6538), *P. aeruginosa* (ATCC 15442), and *E. coli* (ATCC BAA 1427) by serial 2-fold dilution experiments. A solution of chlorhexidine (0.025% w/w) was used as a positive control and comparator. Experiments were performed in triplicate and the average result is shown in Table 3. *S. aureus, P. aeruginosa*, and *E. coli* had ethyl lauroyl arginate hydrochloride (LAE) concentration MBC values (defined as a having less than 500 CFU/mL) of 3.75 μg/mL, 30 μg/mL, and 15 μg/mL, respectively. Overall, the MBC values ranged between 3.75 μg/mL to 30 μg/mL for all tested organisms. This result indicates a great variability in susceptibility to killing (e.g., MBC value variability) by ethyl lauroyl arginate hydrochloride (LAE) between different bacterial species. The control chlorhexidine (0.025% w/w) showed no colonies (e.g., above MBC value for chlorhexidine) for all test organisms.

TABLE 3

Average Bactericidal Testing for Antiseptic Agents

| Antiseptic Agent | Microorganism | Concentration (μg/mL) | Number of Colonies* | Standard Deviation | CFU/mL |
|---|---|---|---|---|---|
| ethyl lauroyl arginate hydrochloride (LAE) | *S. aureus* (ATCC 6538) | 60 | 0 | 0 | 0 |
| | | 30 | 0 | 0 | 0 |
| | | 15 | 0 | 0 | 0 |
| | | 7.5 | 0 | 0 | 0 |
| | | 3.75** | 5 | 2 | 500 |
| | | 1.875 | Lawn | Lawn | Lawn |
| | | 0.9375 | Lawn | Lawn | Lawn |
| | | 0.46875 | Lawn | Lawn | Lawn |
| Chlorhexidine gluconate | | 250 | 0 | 0 | 0 |
| ethyl lauroyl arginate hydrochloride (LAE) | *P. aeruginosa* (ATCC 15442) | 60 | 0 | 0 | 0 |
| | | 30** | 0 | 0 | 0 |
| | | 15 | Lawn | Lawn | Lawn |
| | | 7.5 | Lawn | Lawn | Lawn |
| | | 3.75 | Lawn | Lawn | Lawn |
| | | 1.875 | Lawn | Lawn | Lawn |
| | | 0.9375 | Lawn | Lawn | Lawn |
| | | 0.46875 | Lawn | Lawn | Lawn |
| Chlorhexidine gluconate | | 250 | 0 | 0 | 0 |
| ethyl lauroyl arginate hydrochloride (LAE) | *E. coli* (ATCC BAA 1427) | 60 | 0 | 0 | 0 |
| | | 30 | 0 | 0 | 0 |
| | | 15** | 0 | 0 | 0 |
| | | 7.5 | Lawn | Lawn | Lawn |
| | | 3.75 | Lawn | Lawn | Lawn |
| | | 1.875 | Lawn | Lawn | Lawn |
| | | 0.9375 | Lawn | Lawn | Lawn |
| | | 0.46875 | Lawn | Lawn | Lawn |

TABLE 3-continued

| Average Bactericidal Testing for Antiseptic Agents | | | | | |
|---|---|---|---|---|---|
| Antiseptic Agent | Microorganism | Concentration (μg/mL) | Number of Colonies* | Standard Deviation | CFU/mL |
| Chlorhexidine gluconate | | 250 | 0 | 0 | 0 |

*Number of colonies is average over triplicate experiments. 'Lawn' indicates too many colonies to accurately count (e.g., greater than 250 colonies on an agar plate).
**indicates an MBC value of less than 500 CFU/mL.

Example 5

Fractional Inhibitory Concentration (FIC) and Synergy Analysis of Antiseptic Agents Chlorhexidine gluconate (CHG) and ethyl lauroyl arginate hydrochloride (LAE) were analyzed by chequerboard assay with each test organism to determine potential additive, synergistic, and antagonistic activity. The test organisms *S. aureus, P. aeruginosa*, and *E. coli* were tested at ranges of chlorhexidine gluconate (0.122-15.625 μg/mL, 1.25-160 μg/mL, and 0.125-16 μg/mL, respectively) and ethyl lauroyl arginate hydrochloride (LAE) (0.117-15 μg/mL, 0.4688-60 μg/mL, and 0.2344-30 μg/mL, respectively). The results of the chequerboard experiment are shown in Table 4. FIC was calculated by the following Equation 2:

$$FIC = \frac{LAEMIC \text{ in combination with } CHG}{LAEMIC} + \frac{CHGMIC \text{ in combination with } LAE}{CHGMIC}. \quad \text{(Equation 2)}$$

The results of the synergy analysis (displayed in Table 4) show that the combination of ethyl lauroyl arginate hydrochloride (LAE) and chlorhexidine is synergistic in the inhibition of *P. aeruginosa* as indicated by a FIC of 0.500 (e.g., an FIC equal to or less than about 0.5).

TABLE 4

| Synergy Analysis of ethyl lauroyl arginate hydrochloride (LAE) and Chlorhexidine Gluconate | | | | | |
|---|---|---|---|---|---|
| Test Organism | MIC of CHG Alone (μg/mL) | MIC of LAE Alone (μg/mL) | MIC of CHG in Presence of LAE (μg/mL) | MIC of LAE in Presence of CHG (μg/mL) | Fractional Inhibitory Concentration (FIC) |
| *S. aureus* | 1.953 | 3.75 | 0.977 | 1.875 | 1.000 |
| *P. aeruginosa* | 40 | 30 | 10 | 7.5 | 0.500 |
| *E. coli* | 8 | 15 | 4 | 3.75 | 0.750 |

It should be understood that the examples and embodiments described herein is for illustrative purpose only and that various modifications or changes in light thereof will be suggested to persons skilled in the art and are to be included within the spirit and purview of this application and the scope of the appended claims.

What is claimed is:

1. A method for irrigating a wound comprising the steps of:

(a) providing a non-sterile or sterile wound irrigation solution in a wound irrigation device comprising a reservoir housing, wherein the wound irrigation device comprises a discharge means that directs a pressurized stream of the wound irrigation solution when the reservoir housing is pressurized, and wherein the wound irrigation solution comprises (i) sterile water, purified water, or water for pharmaceutical purposes; (ii) a chlorhexidine at a concentration that is between about 100 μg/mL to about 5 mg/mL, and (iii) lauroyl arginate ethyl ester (LAE) or a pharmaceutically acceptable salt thereof at a concentration that is between about 1 μg/mL to about 200 μg/mL;

(b) directing the discharge means and the reservoir housing so as to discharge the wound irrigation solution toward the wound; and (c) discharging a stream of the wound irrigation solution from the reservoir housing and through the discharge means directed at the wound.

2. The method of claim 1, wherein the chlorhexidine is in the form of chlorhexidine gluconate.

3. The method of claim 1, wherein the concentration of the chlorhexidine is between about 200 μg/mL to about 1 mg/mL or about 100 μg/mL to about 500 μg/mL.

4. The method of claim 1, wherein the concentration of the chlorhexidine is about 500 μg/mL.

5. The method of claim 1, wherein the lauroyl arginate ethyl ester (LAE) or the pharmaceutically acceptable salt thereof is ethyl lauroyl arginate hydrochloride.

6. The method of claim 1, wherein the concentration of the lauroyl arginate ethyl ester (LAE) or the pharmaceutically acceptable salt thereof is between about 2 μg/mL to about 100 μg/mL.

7. The method of claim 1, wherein the concentration of the lauroyl arginate ethyl ester (LAE) or the pharmaceutically acceptable salt thereof is between about 2 μg/mL to about 15 μg/mL or about 10 μg/mL to about 50 μg/mL.

8. The method of claim 1, wherein the concentration of the lauroyl arginate ethyl ester (LAE) or the pharmaceutically acceptable salt thereof is about 7.5 μg/mL or about 30 μg/mL.

9. The method of claim 1, wherein an amount of irrigation time required to reduce a bacterial burden of the wound or a fungal burden of the wound by about 100-fold compared to an analogous method using an alternative irrigation solution comprising the same concentration of chlorhexidine without an additional antiseptic agent is reduced by about 50%.

10. The method of claim 1, wherein the irrigation solution comprises a combination of the chlorhexidine and lauroyl arginate ethyl ester (LAE) or the pharmaceutically acceptable salt thereof that is synergistically microbiocidal or microbiostatic to a fungus or a bacterium.

11. The method of claim 10, wherein the fungus or the bacterium is selected from *Candida* species, *E. coli, Staphylococcus species, Ralstonia species, Pseudomonas* species, or a combination thereof.

12. The method of claim 10, wherein the fungus or the bacterium is *P. aeruginosa.*

13. The method of claim 9, wherein the amount of irrigation time required is within 15 minutes.

14. The method of claim 1, wherein about 10 ml to about 1000 ml of wound irrigation solution is applied to the wound.

15. The method of claim 1, wherein the pH of the wound irrigation solution is between pH 5.5 and pH 7.0.

16. The method of claim 1, used to kill a microorganism selected from the group consisting of *Candida* species, *E. coli, Staphylococcus species, Ralstonia species, Pseudomonas* species, and a combination thereof.

17. The method of claim 1, used to kill *C. albicans, E. coli*, methicillin-resistant *Staphylococcus aureus* (MRSA), *Staphylococcus aureus, Staphylococcus epidermidis, Ralstonia pickettii, P. aeruginosa*, or a combination thereof.

18. The method of claim 1, wherein the wound is a human skin wound and the method is used to treat the human skin wound.

19. The method of claim 1, wherein the wound is selected from the group consisting of cuts, scrapes, surgical wounds, punctures, and abrasions.

* * * * *